United States Patent
Himmelsbach et al.

(10) Patent No.: US 7,375,090 B2
(45) Date of Patent: May 20, 2008

(54) GLUCOPYRANOSYLOXY-PYRAZOLES, PHARMACEUTICAL COMPOSITIONS CONTAINING THESE COMPOUNDS, THE USE THEREOF AND PROCESSED FOR THE PREPARATION THEREOF

(75) Inventors: Frank Himmelsbach, Mittelbiberach (DE); Peter Eickelmann, Mittelbiberach (DE); Leo Thomas, Biberach (DE); Edward Leon Barsoumian, Toyonaka (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 412 days.

(21) Appl. No.: 10/925,656

(22) Filed: Aug. 24, 2004

(65) Prior Publication Data

US 2005/0233982 A1    Oct. 20, 2005

Related U.S. Application Data

(60) Provisional application No. 60/538,559, filed on Jan. 23, 2004, provisional application No. 60/503,120, filed on Sep. 15, 2003.

(30) Foreign Application Priority Data

Aug. 26, 2003  (DE) ................. 103 39 549
Dec. 18, 2003  (DE) ................. 103 59 960

(51) Int. Cl.
*A01N 43/04* (2006.01)
*A61K 31/70* (2006.01)
*C07H 15/00* (2006.01)
*C07H 17/00* (2006.01)
*C07G 3/00* (2006.01)

(52) U.S. Cl. .............. 514/27; 514/25; 536/17.2; 536/17.3; 536/17.4; 536/18.1; 536/18.5

(58) Field of Classification Search ............ None
See application file for complete search history.

(56) References Cited

U.S. PATENT DOCUMENTS

| 6,972,283 | B2 | 12/2005 | Fujikura et al. |
| 7,045,665 | B2 | 5/2006 | Fujikura et al. |
| 7,056,892 | B2 | 6/2006 | Fujikura et al. |
| 7,115,575 | B2 | 10/2006 | Fujikura et al. |
| 7,256,209 | B2 | 8/2007 | Ohsumi et al. |
| 2004/0063646 | A1 | 4/2004 | Fujikura et al. |
| 2004/0110936 | A1 | 6/2004 | Ohsumi et al. |
| 2004/0116357 | A1 | 6/2004 | Fushimi et al. |
| 2004/0132669 | A1 | 7/2004 | Nishimura et al. |
| 2004/0176308 | A1 | 9/2004 | Shiohara et al. |
| 2005/0272669 | A1* | 12/2005 | Fushimi et al. ............. 514/23 |
| 2007/0060531 | A1 | 3/2007 | Kikuchi et al. |

FOREIGN PATENT DOCUMENTS

| CA | 2 484 306 A1 | 11/2003 |
| WO | 01/16147 A1 | 3/2001 |
| WO | 01/27128 A1 | 4/2001 |
| WO | 01/68660 A1 | 9/2001 |
| WO | 02/36602 A1 | 5/2002 |
| WO | 02/098893 A1 | 12/2002 |
| WO | 03/020737 A1 | 3/2003 |
| WO | 03/090783 A1 | 11/2003 |
| WO | 2004/019958 A1 | 3/2004 |
| WO | 2004/113359 A1 | 12/2004 |
| WO | 2007/010015 A1 | 1/2007 |
| WO | 2007/014895 A2 | 2/2007 |

* cited by examiner

*Primary Examiner*—Shaojia Anna Jiang
*Assistant Examiner*—Traviss C. McIntosh, III
(74) *Attorney, Agent, or Firm*—Michael Morris; David Dow; Mary-Ellen M. Devlin

(57) ABSTRACT

The present invention relates to glucopyranosyloxy-pyrazoles of general formula

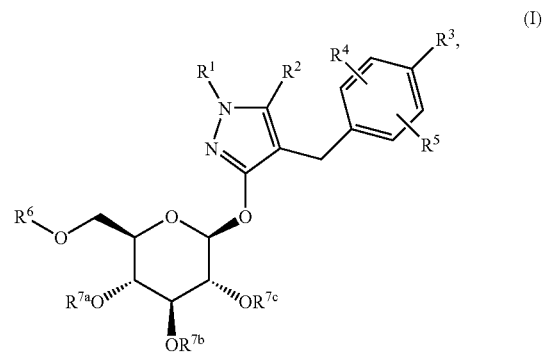

wherein
$R^1$ to $R^6$ and $R^{7a}$, $R^{7b}$, $R^{7c}$ are defined as in claim 1, the tautomers, the stereoisomers, the mixtures thereof and the salts thereof, particularly the physiologically acceptable salts thereof with inorganic or organic acids, which have valuable pharmacological properties, particularly an inhibitory effect on sodium-dependent glucose cotransporter SGLT, the use thereof for the treatment of diseases, particularly metabolic disorders such as diabetes, and the preparation thereof.

26 Claims, No Drawings

GLUCOPYRANOSYLOXY-PYRAZOLES, PHARMACEUTICAL COMPOSITIONS CONTAINING THESE COMPOUNDS, THE USE THEREOF AND PROCESSED FOR THE PREPARATION THEREOF

RELATED APPLICATIONS

This application claims priority benefit of U.S. Ser. No. 60/503,120, filed Sep. 15, 2003; U.S. Ser. No. 60/538,559, filed Jan. 23, 2004; German Application No. 103 39 549.0, filed Aug. 26, 2003; and German Application 103 59 960.6, filed Dec. 18, 2003, each of which is hereby incorporated by reference in its entirety.

BACKGROUND OF THE INVENTION

The present invention relates to glucopyranosyloxy-pyrazoles of general formula I

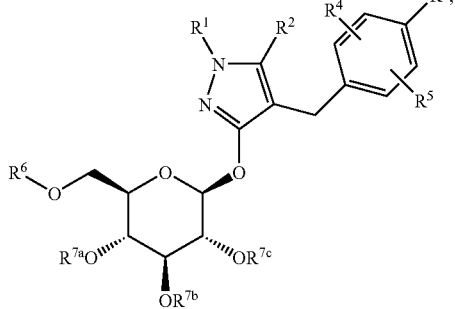

(I)

wherein the groups $R^1$ to $R^6$ and $R^{7a}$, $R^{7b}$, $R^{7c}$ are defined hereinafter, including the tautomers, the stereoisomers, the mixtures thereof and the salts thereof. The invention also relates to pharmaceutical compositions containing a compound of formula I according to the invention as well as the use of a compound according to the invention for preparing a pharmaceutical composition for the treatment of metabolic disorders. Processes for preparing a pharmaceutical composition and a compound according to the invention are also the subject of this invention.

In the literature, compounds which have an inhibitory effect on the sodium-dependent glucose cotransporter SGLT2 are proposed for the treatment of diseases, particularly diabetes.

Glucopyranosyloxy-pyrazole derivatives and the preparation thereof and their possible activity as SGLT2 inhibitors are known from published International applications WO 02/36602, WO 02/088157, WO 01/16147, WO 02/053573, WO 02/068439, WO 02/068440 and WO 02/098893.

AIM OF THE INVENTION

The aim of the present invention is to find new glucopyranosyloxy-pyrazole derivatives, particularly those which are active with regard to the sodium-dependent glucose cotransporter SGLT, particularly SGLT2. A further aim of the present invention is to discover glucopyranosyloxy-pyrazole derivatives which have an enhanced inhibitory effect on the sodium-dependent glucose cotransporter SGLT2 in vitro and/or in vivo compared with known, structurally similar glucopyranosyloxy-pyrazoles and/or have better pharmacological properties.

A further aim of the present invention is to provide new pharmaceutical compositions which are suitable for the prevention and/or treatment of metabolic disorders, particularly diabetes.

The invention also sets out to provide a process for preparing the compounds according to the invention.

Other aims of the present invention will become apparent to the skilled artisan directly from the foregoing and following remarks.

OBJECT OF THE INVENTION

In a first aspect the present invention relates to glucopyranosyloxy-pyrazoles of general formula I

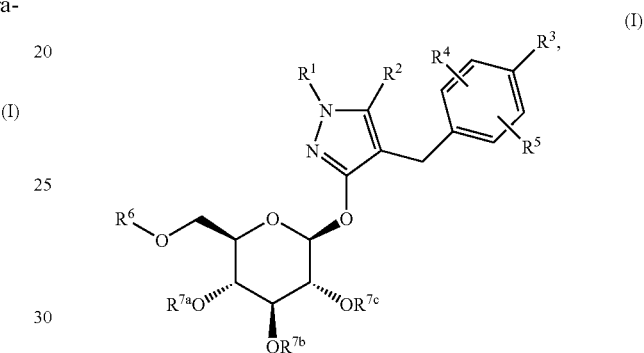

(I)

wherein
$R^1$ denotes $C_{3-6}$-alkynyl, tetrahydrofuran-3-yl, tetrahydropyran-3-yl, tetrahydropyran-4-yl, tetrahydrofuranyl-$C_{1-3}$-alkyl, tetrahydropyranyl-$C_{1-3}$-alkyl, pyrrolidin-3-yl, piperidin-3-yl, piperidin-4-yl, or
a pyrrolidin-3-yl, piperidin-3-yl or piperidin-4-yl group, while in the latter three groups the nitrogen atom may be substituted by a $C_{1-4}$-alkyl, formyl, $C_{1-4}$-alkyl-carbonyl, $C_{1-4}$-alkylsulphonyl, cyano, aminocarbonyl, ($C_{1-4}$-alkyl)-aminocarbonyl, di-($C_{1-4}$-alkyl)-aminocarbonyl or ($C_{1-4}$-alkyl)-oxycarbonyl group, or
if $R^3$
  (a) is selected from one of the definitions of the group A; or
  (b) together with $R^4$ denotes difluoromethylenedioxy; or
  (c) denotes $C_{3-4}$-cycloalkyl-oxy or $C_{3-6}$-cycloalkylidenemethyl and simultaneously $R^4$ denotes fluorine, chlorine, bromine, $C_{1-3}$-alkyl, $C_{1-3}$-alkoxy or a methyl or methoxy group substituted by 1 to 3 fluorine atoms;
  then $R^1$ may also represent hydrogen, $C_{1-6}$-alkyl, a $C_{1-4}$-alkyl group substituted by 1 to 3 fluorine atoms, a $C_{2-4}$-alkyl group substituted by a hydroxy or $C_{1-3}$-alkoxy group, or $C_{3-6}$-alkenyl, $C_{3-6}$-cycloalkyl, $C_{3-6}$-cycloalkyl-$C_{1-3}$-alkyl, aryl or aryl-$C_{1-3}$-alkyl, and
$R^2$ denotes $C_{1-4}$-alkyl, a $C_{1-4}$-alkyl group substituted by 1 to 3 fluorine atoms, or $C_{3-6}$-cycloalkyl, and
$R^3$ denotes hydrogen, fluorine, chlorine, bromine, iodine, $C_{1-6}$-alkyl, $C_{2-6}$-alkenyl, $C_{2-6}$-alkynyl, $C_{3-6}$-cycloalkyl, $C_{3-6}$-cycloalkylidenemethyl, $C_{1-6}$-alkoxy, $C_{3-6}$-cycloalkyl-oxy, $C_{3-6}$-cycloalkyl-$C_{1-3}$-alkoxy, aryl, aryl-$C_{1-3}$-alkyl, heteroaryl, heteroaryl-$C_{1-3}$-alkyl, aryloxy, aryl-$C_{1-3}$-alkyl-oxy, a methyl or methoxy group substituted by 1 to 3 fluorine atoms, a $C_{2-4}$-alkyl or $C_{2-4}$-alkoxy group substituted by 1 to 5 fluorine atoms, a $C_{1-4}$-alkyl group substituted by a cyano group, a $C_{1-4}$-alkyl group substituted by a hydroxy or $C_{1-3}$-alkyloxy group, or cyano, carboxy, $C_{1-3}$-alkoxycarbonyl, aminocarbonyl, ($C_{1-3}$-alkylamino)carbonyl, di-($C_{1-3}$-alkyl)aminocarbonyl, pyrrolidin-1-ylcarbonyl, piperidin-1-ylcarbonyl, morpholin-4-ylcarbonyl, piperazin-1-yl-carbonyl, 4-($C_{1-3}$-alkyl)-piperazin-1-ylcarbonyl, nitro, amino, $C_{1-3}$-alkylamino, di-($C_{1-3}$-alkyl)amino, ($C_{1-4}$-alkyl)carbonylamino, $C_{1-4}$-alkylsulphonylamino, arylsulphonylamino, aryl-$C_{1-3}$-alkylsulphonylamino, $C_{1-4}$-alkylsulphanyl, $C_{1-4}$-alkylsulphinyl, $C_{1-4}$-alkylsulphonyl, arylsulphenyl, arylsulphinyl or arylsulphonyl, or has a meaning selected from the group A, and $R^4$ and $R^5$, which may be identical or different, represent hydrogen, fluorine, chlorine, bromine, $C_{1-3}$-alkyl, $C_{1-3}$-alkoxy, a methyl or methoxy group substituted by 1 to 3 fluorine atoms, or $R^3$ together with $R^4$, if they are bound to adjacent carbon atoms, may also represent a straight-chain $C_{3-5}$-alkylene, a methylenedioxy or difluoromethylenedioxy bridge, and $R^6$, $R^{7a}$, $R^{7b}$, $R^{7c}$ independently of one another have a meaning selected from the group hydrogen, ($C_{1-18}$-alkyl)carbonyl, ($C_{1-18}$-alkyl)oxycarbonyl, arylcarbonyl and aryl-($C_{1-3}$-alkyl)-carbonyl, A is selected from the group consisting of tetrahydrofuran-3-yloxy, tetrahydropyran-3-yloxy, tetrahydropyran-4-yloxy, tetrahydrofuranyl-$C_{1-3}$-alkoxy, tetrahydropyranyl-$C_{1-3}$-alkoxy, pyrrolidin-3-yloxy, piperidin-3-yloxy, piperidin-4-yloxy group, and pyrrolidin-3-yloxy, piperidin-3-yloxy- and piperidin-4-yloxy, while in the latter three groups the nitrogen atom may be substituted by $C_{1-4}$-alkyl, formyl, $C_{1-4}$-alkylcarbonyl, $C_{1-4}$-alkylsulphonyl, cyano, aminocarbonyl, ($C_{1-4}$-alkyl)-aminocarbonyl, di-($C_{1-4}$-alkyl)-aminocarbonyl or ($C_{1-4}$-alkyl)-oxycarbonyl, while the aryl groups mentioned in the definition of the above groups are meant to indicate phenyl or naphthyl groups which may be mono- or disubstituted independently of one another by $R_h$, while the substituents may be identical or different and $R_h$ denotes a fluorine, chlorine, bromine, iodine, $C_{1-3}$-alkyl, difluoromethyl, trifluoromethyl, $C_{1-3}$-alkoxy, difluoromethoxy, trifluoromethoxy or cyano, the heteroaryl groups mentioned in the definition of the above-mentioned groups are meant to indicate a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted by $R_h$, while the substituents may be identical or different and $R_h$ is as hereinbefore defined, while, unless otherwise stated, the above-mentioned alkyl groups may be straight-chain or branched, the tautomers, the stereoisomers, the mixtures thereof and the salts thereof, particularly the physiologically acceptable salts thereof.

The compounds according to the invention of general formula I and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

Therefore, the invention also relates to the use of the compounds according to the invention, including the physiologically acceptable salts, as pharmaceutical compositions.

This invention also relates to pharmaceutical compositions, containing at least one compound according to the invention or a physiologically acceptable salt according to the invention, optionally together with one or more inert carriers and/or diluents.

A further subject of this invention is the use of at least one compound according to the invention or a physiologically acceptable salt of such a compound for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention for preparing a pharmaceutical composition which is suitable for the treatment of metabolic disorders.

This invention also relates to the use of at least one compound according to the invention for preparing a pharmaceutical composition for inhibiting the sodium-dependent glucose cotransporter SGLT, particularly SGLT2.

The invention further relates to a process for preparing a pharmaceutical composition according to the invention, characterised in that a compound according to the invention is incorporated in one or more inert carriers and/or diluents by a non-chemical method.

The present invention also relates to a process for preparing the compounds according to the invention of general formula I, characterised in that a) in order to prepare compounds of general formula I wherein $R^1$ is as hereinbefore defined, but does not denote hydrogen, a compound of general formula

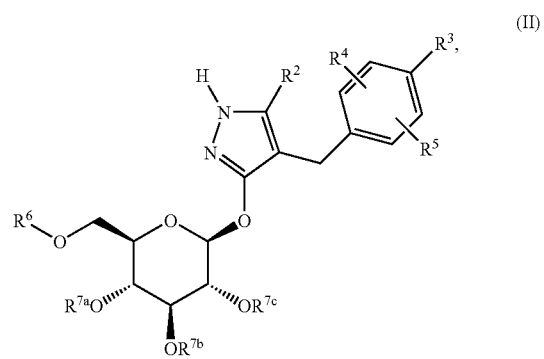

(II)

wherein $R^2$ to $R^6$ and $R^{7a}$, $R^{7b}$, $R^{7c}$ are as hereinbefore defined, is reacted with a compound of general formula $$Z^1\text{—}R^{1'} \qquad (III),$$

wherein $R^{1'}$ has the meanings given for $R^1$ hereinbefore, but does not denote a hydrogen atom, and $Z^1$ denotes a leaving group, or b) in order to prepare compounds of general formula I wherein $R^3$ denotes optionally substituted $C_{1-6}$-alkoxy, $C_{3-6}$-cycloalkyl-oxy, $C_{3-5}$-cycloalkyl-$C_{1-3}$-alkoxy or a meaning selected from the group A, which is as hereinbefore defined, a compound of general formula (IV)

wherein $R^1$, $R^2$ and $R^4$ to $R^6$ as well as $R^{7a}$, $R^{7b}$, $R^{7c}$ are as hereinbefore defined, is reacted with a compound of general formula $$Z^2\text{—}R^{3'} \qquad (V)$$

wherein $R^3$ denotes optionally substituted $C_{1-6}$-alkoxy, $C_{3-6}$-cycloalkyl-oxy, $C_{3-5}$-cycloalkyl-$C_{1-3}$-alkoxy or a meaning selected from the group A, which is as hereinbefore defined, and $Z^2$ denotes a leaving group, preferably a halogen atom, for example a chlorine or bromine atom, a sulphonyloxy group, for example a methanesulphonyloxy or p-toluene-sulphonyloxy group or a hydroxy group, and after step a) or b) has been carried out, if desired a compound of general formula I thus obtained wherein $R^6$ denotes a hydrogen atom, is converted by acylation into a corresponding acyl compound of general formula I, and/or if necessary a protecting group used during the reactions described above is cleaved again and/or if desired a compound of general formula I thus obtained is separated into its stereoisomers and/or a compound of general formula I thus obtained is converted into the salts thereof, particularly for pharmaceutical use into the physiologically acceptable salts thereof.

DETAILED DESCRIPTION OF THE INVENTION

Unless otherwise stated the groups, residues and substituents, particularly $R^1$ to $R^6$ and $R^{7a}$, $R^{7b}$, $R^{7c}$, are defined as above and hereinafter.

If residues, substituents or groups occur several times in a compound, they may have the same or different meanings.

The term aryl used above and hereinafter, for example in the groups $R^1$, $R^3$, $R^6$, $R^{7a}$, $R^{7b}$, $R^{7c}$, preferably denotes phenyl. According to the general definition and unless otherwise stated, the aryl group, particularly the phenyl group, may be mono- or disubstituted by identical or different groups $R_h$.

Compounds according to the invention, in a first embodiment of this invention, may be described by general formula I, wherein $R^1$ denotes $C_{3-6}$-alkynyl, tetrahydrofuran-3-yl, tetrahydropyran-3-yl, tetrahydropyran-4-yl, tetrahydrofuranyl-$C_{1-3}$-alkyl, tetrahydropyranyl-$C_{1-3}$-alkyl, pyrrolidin-3-yl, piperidin-3-yl, piperidin-4-yl, or a pyrrolidin-3-yl, piperidin-3-yl or piperidin-4-yl group, while in the latter three groups the nitrogen atom may be substituted by a $C_{1-4}$-alkyl, formyl, $C_{1-4}$-alkyl-carbonyl, $C_{1-4}$-alkylsulphonyl, cyano, aminocarbonyl, ($C_{1-4}$-alkyl)-aminocarbonyl, di-($C_{1-4}$-alkyl)-aminocarbonyl or ($C_{1-4}$-alkyl)-oxycarbonyl group, and the other groups $R^2$ to $R^6$ and $R^{7a}$, $R^{7b}$, $R^{7c}$ are as hereinbefore defined, including the tautomers, the stereoisomers, the mixtures thereof and the salts thereof.

Preferred meanings of the group $R^1$ according to this embodiment are 2-propyn-1-yl, 2-butyn-1-yl, tetrahydrofuran-3-yl, tetrahydropyran-3-yl, tetrahydropyran-4-yl, tetrahydrofuranylmethyl and tetrahydropyranylmethyl. Most particularly preferred meanings are 2-propyn-1-yl, 2-butyn-1-yl, tetrahydrofuran-3-yl, tetrahydropyran-4-yl- and tetrahydrofuran-2-ylmethyl.

Preferred meanings of the group $R^3$ according to this embodiment are hydrogen, fluorine, chlorine, methyl, ethyl, isopropyl, tert.-butyl, 2-cyano-2-propyl, difluoromethyl, trifluoromethyl, cyclopropyl, cyclobutyl, cyclopentyl, methoxy, ethoxy, isopropoxy, difluoromethoxy, trifluoromethoxy, 1,1,2,2-tetrafluoroethoxy, cyclopropyl-oxy, cyclobutyl-oxy, cyclopentyl-oxy, tetrahydrofuran-3-yloxy, tetrahydropyran-3-yloxy, tetrahydropyran-4-yloxy, tetrahydrofuranyl methyloxy, tetrahydropyranyl-methyloxy, methylsulphanyl, 2-methyl-1-propen-1-yl, cyclopropylidenemethyl, ethynyl, phenyl, fluorophenyl, pyridyl and methylthiazolyl. Most particularly preferred meanings are fluorine, chlorine, methyl, ethyl, isopropyl, tert.-butyl, difluoromethyl, trifluoromethyl, cyclopropyl, cyclobutyl, cyclopentyl, methoxy, ethoxy, isopropoxy, difluoromethoxy, trifluoromethoxy, particularly ethyl.

Preferred meanings of the group $R^4$ according to this first embodiment are hydrogen and fluorine, particularly hydrogen.

Compounds according to the invention in a second embodiment of this invention may be described by general formula I, wherein $R^1$ denotes hydrogen, $C_{1-6}$-alkyl, $C_{1-4}$-alkyl substituted by 1 to 3 fluorine atoms, $C_{2-4}$-alkyl substituted by a hydroxy or $C_{1-3}$-alkoxy group, $C_{3-6}$-alkenyl, $C_{3-6}$-cycloalkyl, $C_{3-6}$-cycloalkyl-$C_{1-3}$-alkyl, aryl or aryl-$C_{1-3}$-alkyl, and $R^3$ is selected from the group A consisting of tetrahydrofuran-3-yloxy, tetrahydropyran-3-yloxy, tetrahydropyran-4-yloxy, tetrahydrofuranyl-$C_{1-3}$-alkoxy, tetrahydropyranyl-$C_{1-3}$-alkoxy, pyrrolidin-3-yloxy, piperidin-3-yloxy, piperidin-4-yloxy group, and pyrrolidin-3-yloxy, piperidin-3-yloxy and piperidin-4-yloxy, while in the latter three groups the nitrogen atom is substituted by $C_{1-4}$-alkyl, formyl, $C_{1-4}$-alkyl-carbonyl, $C_{1-4}$-alkylsulphonyl, cyano, aminocarbonyl, $(C_{1-4}$-alkyl)-aminocarbonyl, di-$(C_{1-4}$-alkyl)-aminocarbonyl or $(C_{1-4}$-alkyl)-oxycarbonyl, and the other groups, particularly $R^2$ and $R^4$ to $R^6$ and $R^{7a}$, $R^{7b}$, $R^{7c}$ are as hereinbefore defined, including the tautomers, the stereoisomers, the mixtures thereof and the salts thereof.

Preferred meanings of the group $R^1$ according to this embodiment are $C_{1-6}$alkyl, a $C_{1-4}$-alkyl group substituted by 1 to 3 fluorine atoms, $C_{3-4}$-cycloalkyl and $C_{3-6}$-cycloalkyl-$C_{1-3}$-alkyl, particularly $C_{1-4}$-alkyl, which may be substituted by 1 to 3 fluorine atoms, most preferably methyl, ethyl, propyl or butyl, most particularly preferably isopropyl.

Preferred meanings of the group $R^3$ according to this embodiment are tetrahydrofuran-3-yloxy, tetrahydropyran-3-yloxy, tetrahydropyran-4-yloxy, tetrahydrofuranylmethyloxy and tetrahydropyranylmethyloxy.

Preferred meanings of the group $R^4$ according to this second embodiment are hydrogen and fluorine, particularly hydrogen.

Compounds according to the invention in accordance with a third embodiment of this invention may be described by general formula I, wherein $R^1$ denotes hydrogen, $C_{1-6}$-alkyl,
  $C_{1-4}$-alkyl substituted by 1 to 3 fluorine atoms,
  $C_{2-4}$-alkyl substituted by a hydroxy or $C_{1-3}$-alkoxy group,
  $C_{3-4}$-alkenyl, $C_{3-6}$-cycloalkyl, $C_{3-6}$-cycloalkyl-$C_{1-3}$-alkyl, aryl or aryl-$C_{1-3}$-alkyl, and
$R^3$ together with $R^4$, which are bound to adjacent carbon atoms, denotes a difluoromethylenedioxy bridge, and the other groups, particularly $R^2$, $R^5$ and $R^6$ and $R^{7a}$, $R^{7b}$, $R^{7c}$ are as hereinbefore defined, including the tautomers, the stereoisomers, the mixtures thereof and the salts thereof.

Preferred meanings of the group $R^1$ according to this embodiment are $C_{1-6}$-alkyl, a $C_{1-4}$-alkyl group substituted by 1 to 3 fluorine atoms, $C_{3-6}$-cycloalkyl and $C_{3-6}$-cycloalkyl-$C_{1-3}$-alkyl, particularly $C_{1-4}$-alkyl, which may be substituted by 1 to 3 fluorine atoms, particularly preferably methyl, ethyl, propyl or butyl, most particularly preferably isopropyl.

Compounds according to the invention in a fourth embodiment of this invention may be described by general formula I, wherein $R^1$ denotes hydrogen, $C_{1-6}$-alkyl,
  $C_{1-4}$-alkyl substituted by 1 to 3 fluorine atoms,
  $C_{2-4}$-alkyl substituted by a hydroxy or $C_{1-3}$-alkoxy group,
  $C_{3-6}$-alkenyl, $C_{3-6}$-cycloalkyl, $C_{3-6}$-cycloalkyl-$C_{1-3}$-alkyl, aryl or aryl-$C_{1-3}$-alkyl, and
$R^3$ denotes $C_{3-6}$-cycloalkyl-oxy, and
$R^4$ denotes fluorine, chlorine, bromine, $C_{1-3}$-alkyl, $C_{1-3}$-alkoxy or a methyl or methoxy group substituted by 1 to 3 fluorine atoms, and the other groups, particularly $R^2$, $R^5$ and $R^6$ as well as $R^{7a}$, $R^{7b}$, $R^{7c}$ are as hereinbefore defined, including the tautomers, the stereoisomers, the mixtures thereof and the salts thereof.

Preferred meanings of the group $R^1$ according to this embodiment are $C_{1-6}$-alkyl, a $C_{1-4}$-alkyl group substituted by 1 to 3 fluorine atoms, $C_{3-6}$-cycloalkyl and $C_{3-6}$-cycloalkyl-$C_{1-3}$-alkyl, particularly $C_{1-4}$-alkyl, which may be substituted by 1 to 3 fluorine atoms, particularly preferably methyl, ethyl, propyl or butyl, most particularly preferably isopropyl.

Preferred meanings of the group $R^3$ according to this embodiment are cylopropyloxy, cyclobutyloxy and cyclopentyloxy.

Preferred meanings of the group $R^4$ according to this embodiment are fluorine, chlorine, bromine, methyl, trifluoromethyl, methoxy and trifluoromethoxy, particularly fluorine.

Compounds according to the invention in a fifth embodiment of this invention may be described by general formula I, wherein $R^1$ denotes hydrogen, $C_{1-6}$-alkyl,
  $C_{1-4}$-alkyl substituted by 1 to 3 fluorine atoms,
  $C_{2-4}$-alkyl substituted by a hydroxy or $C_{1-3}$-alkoxy group,
  $C_{3-6}$-alkenyl, $C_{3-6}$-cycloalkyl, $C_{3-6}$-cycloalkyl-$C_{1-3}$-alkyl, aryl or aryl-$C_{1-3}$-alkyl, and
$R^3$ denotes $C_{3-6}$-cycloalkylidene-methyl, and
$R^4$ denotes fluorine, chlorine, bromine, $C_{1-3}$-alkyl, $C_{1-3}$-alkoxy or a methyl or methoxy group substituted by 1 to 3 fluorine atoms, and the other groups, particularly $R^2$, $R^5$ and $R^6$ and $R^{7a}$, $R^{7b}$, $R^{7c}$ are as hereinbefore defined, including the tautomers, the stereoisomers, the mixtures thereof and the salts thereof.

Preferred meanings of the group $R^1$ according to this embodiment are $C_{1-6}$-alkyl, $C_{1-4}$-alkyl substituted by 1 to 3 fluorine atoms, $C_{3-6}$-cycloalkyl and $C_{3-6}$-cycloalkyl-$C_{1-3}$-alkyl, particularly $C_{1-4}$-alkyl, which may be substituted by 1 to 3 fluorine atoms, particularly preferably methyl, ethyl, propyl or butyl, most particularly preferably isopropyl.

A preferred meaning of the group $R^3$ according to this embodiment is cyclopropylidenemethyl.

Preferred meanings of the group $R^4$ according to this embodiment are fluorine, chlorine, bromine, methyl, trifluoromethyl, methoxy and trifluoromethoxy, particularly fluorine.

The following remarks refer to the compounds of formula I, particularly the first, second, third, fourth and fifth embodiments already mentioned above.

If the group $R^1$ denotes pyrrolidin-3-yl, piperidin-3-yl or piperidin-4-yl, the nitrogen atom is preferably substituted as specified.

According to an alternative to the embodiments described above, other preferred compounds are those wherein the phenyl group which carries the substituents $R^3$, has at least one other substituent $R^4$ and/or $R^5$ which is not hydrogen. According to this alternative, particularly preferred compounds are those which have a substituent $R^4$ which is fluorine.

Preferred meanings of the group $R^5$ are hydrogen and fluorine.

Preferred meanings of the group $R^2$ according to the invention are methyl and trifluoromethyl, particularly methyl.

The group $R^6$ according to the invention preferably denotes hydrogen, $(C_{1-8}$-alkyl)oxycarbonyl or $C_{1-8}$-alkylcarbonyl, particularly H or $(C_{1-6}$-alkyl)oxycarbonyl, particularly preferably H, methoxycarbonyl or ethoxycarbonyl.

The substituents $R^{7a}$, $R^{7b}$, $R^{7c}$ independently of one another preferably represent hydrogen or $(C_{1-18}$-alkyl)carbonyl, particularly hydrogen or $(C_{1-8}$-alkyl)carbonyl, particularly preferably hydrogen, methylcarbonyl or ethylcarbonyl. Most preferably, $R^{7a}$, $R^{7b}$ and $R^{7c}$ represent hydrogen.

The compounds of formula I wherein $R^6$, $R^{7a}$, $R^{7b}$ and $R^{7c}$ have a meaning according to the invention other than H, for example $C_{1-8}$-alkylcarbonyl, are preferred as intermediate products for the synthesis of compounds of formula I wherein $R^{7a}$, $R^{7b}$ and $R^{7c}$ represent hydrogen.

According to the invention compounds of general formula I are preferred wherein $R^1$ denotes 2-propyn-1-yl, 2-butyn-1-yl, tetrahydrofuran-3-yl, tetrahydropyran-3-yl, tetrahydropyran-4-yl, tetrahydrofuranylmethyl or tetrahydropyranylmethyl, or,
if $R^3$
  (a) is selected from the group consisting of tetrahydrofuran-3-yloxy, tetrahydropyran-3-yloxy, tetrahydropyran-4-yloxy, tetrahydrofuranylmethyloxy and tetrahydropyranylmethyloxy, or
  (b) together with $R^4$ denotes a difluoromethylenedioxy bridge, or,
  (c) denotes cylopropyloxy, cyclobutyloxy, cyclopentyloxy or cyclopropylidenemethyl and $R^4$ simultaneously denotes fluorine,
then $R^1$ may also represent isopropyl, and $R^2$ denotes methyl or trifluoromethyl, $R^3$ denotes hydrogen, fluorine, chlorine, methyl, ethyl, isopropyl, tert.-butyl, 2-cyano-2-propyl, difluoromethyl, trifluoromethyl, cyclopropyl, cyclobutyl, cyclopentyl, methoxy, ethoxy, isopropoxy, difluoromethoxy, trifluoromethoxy, 1,1,2,2-tetrafluoroethoxy, cylopropyloxy, cyclobutyl-oxy, cyclopentyl-oxy, tetrahydrofuran-3-yloxy, tetrahydropyran-3-yloxy, tetrahydropyran-4-yloxy, tetrahydrofuranylmethyloxy, tetrahydropyranylmethyloxy, methylsulphanyl, 2-methyl-1-propen-1-yl, cyclopropylidenemethyl, ethynyl, phenyl, fluorophenyl, pyridyl or methylthiazolyl, and $R^4$ denotes hydrogen or fluorine, or $R^3$ together with $R^4$, if they are bound to adjacent carbon atoms, may also represent a 1,3-propylene, methylenedioxy or difluoromethylenedioxy bridge, and $R^5$ denotes hydrogen and $R^6$ denotes hydrogen, $(C_{1-8}$-alkyl)oxycarbonyl or $C_{1-8}$-alkylcarbonyl, the tautomers, the stereoisomers, the mixtures thereof and the salts thereof.

According to the invention compounds of general formula I are particularly preferred wherein $R^1$ denotes 2-propyn-1-yl, 2-butyn-1-yl, tetrahydrofuran-3-yl, tetrahydropyran-4-yl or tetrahydrofuran-2-ylmethyl or, if $R^3$
  is selected from the group consisting of tetrahydrofuran-3-yloxy, tetrahydropyran-4-yloxy and tetrahydrofuranylmethyloxy,
then $R^1$ may also represent isopropyl, $R^2$ denotes methyl, $R^3$ denotes methyl, ethyl, methoxy, ethoxy, difluoromethoxy, tetrahydrofuran-3-yloxy, tetrahydropyran-4-yloxy or tetrahydrofuranylmethyloxy, $R^4$ denotes hydrogen or fluorine $R^5$ denotes hydrogen and $R^6$ denotes hydrogen, methoxycarbonyl or ethoxycarbonyl, the tautomers, the stereoisomers, the mixtures thereof and the salts thereof.

According to the invention compounds of general formula I are most particularly preferred, wherein $R^1$ denotes tetrahydrofuran-3-yl or tetrahydropyran-4-yl, $R^2$ denotes methyl, $R^3$ denotes methyl, ethyl, methoxy, ethoxy or difluoromethoxy, $R^4$ denotes hydrogen or fluorine, $R^5$ denotes hydrogen, $R^6$ denotes hydrogen, methoxycarbonyl or ethoxycarbonyl and $R^{7a}$, $R^{7b}$ and $R^{7c}$ represent hydrogen, the tautomers, the stereoisomers, the mixtures thereof and the salts thereof.

Particularly preferred compounds of general formula I are selected from the group:

(a) 1-(2-propyn-1-yl)-3-(β-D-glucopyranosyloxy)-4-(4-ethylbenzyl)-5-methyl-1H-pyrazole (b) 1-(2-propyn-1-yl)-3-(6-O-methoxycarbonyl-β-D-glucopyranosyloxy)-4-(4-ethylbenzyl)-5-methyl-1H-pyrazole (c) 1-((S)-tetrahydrofuran-3-yl)-3-(β-D-glucopyranosyloxy)-4-(4-ethylbenzyl)-5-methyl-1H-pyrazole (d) 1-(tetrahydropyran-4-yl)-3-(β-D-glucopyranosyloxy)-4-(4-ethylbenzyl)-5-methyl-1H-pyrazole, (e) 1-isopropyl-3-(β-D-glucopyranosyloxy)-4-[4-((S)-tetrahydrofuran-3-yloxy)benzyl]-5-methyl-1H-pyrazole (f) 1-isopropyl-3-(β-D-glucopyranosyloxy)-4-[4-((R)-tetrahydrofuran-3-yloxy)benzyl]-5-methyl-1H-pyrazole, (g) 1-(tetrahydropyran-4-yl)-3-(β-D-glucopyranosyloxy)-4-(4-methoxybenzyl)-5-methyl-1H-pyrazole, and the derivatives thereof, wherein $R^6$ has a meaning according to the invention other than hydrogen, and in particular $R^6$ denotes ethoxycarbonyl or methoxycarbonyl, including the tautomers, the stereoisomers, the mixtures thereof and the salts thereof.

Some terms used above and hereinafter to describe the compounds according to the invention will now be defined more closely.

The term halogen denotes an atom selected from the group consisting of F, Cl, Br and I, particularly F, Cl and Br.

The term $C_{1-n}$-alkyl, wherein n may have a value of 2 to 8, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{1-n}$-alkylene, wherein n may have a value of 2 to 8, denotes a saturated, branched or unbranched hydrocarbon bridge with 1 to n C atoms. Examples of such groups include methylene (—CH$_2$—), ethylene (—CH$_2$—CH$_2$—), 1-methyl-ethylene (—CH(CH$_3$)—CH$_2$—), 1,1-dimethyl-ethylene (—C(CH$_3$)$_2$—CH$_2$—), n-prop-1,3-ylene (—CH$_2$—CH$_2$—CH$_2$—), 1-methylprop-1,3-ylene (—CH(CH$_3$)—CH$_2$—CH$_2$—), 2-methylprop-1,3-ylene (—CH$_2$—CH(CH$_3$)—CH$_2$—), etc., as well as the corresponding mirror-symmetrical forms.

The term $C_{2-n}$-alkenyl, wherein n has a value of 3 to 6, denotes a branched or unbranched hydrocarbon group with 2 to n C atoms and a C=C-double bond. Examples of such groups include vinyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, iso-propynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl etc.

The term $C_{1-n}$-alkoxy or $C_{1-n}$-alkyloxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a monounsaturated mono-, bi-, tri- or spirocarbocyclic group with 5 to n C atoms. Examples of such groups include cyclopentenyl, cyclohexenyl, cycloheptenyl, cyclooctenyl, cyclononenyl, etc.

The term $C_{3-n}$-cycloalkyloxy denotes a $C_{3-n}$-cycloalkyl-O group, wherein $C_{3-n}$-cycloalkyl is as hereinbefore defined. Examples of such groups include cyclopropyloxy, cyclobutyloxy, cyclopentyloxy, cyclohexyloxy, cycloheptyloxy, etc.

The term $C_{3-n}$-cycloalkylcarbonyl denotes a $C_{3-n}$-cycloalkyl-C(=O) group, wherein $C_{3-n}$-cycloalkyl is as hereinbefore defined.

The style used above and hereinafter, in which a bond of a substituent in a phenyl group is shown towards the centre of the phenyl ring, denotes, unless otherwise stated, that this substituent may be bound to any free position of the phenyl ring bearing an H atom.

The compounds according to the invention may be obtained using methods of synthesis known in principle. Preferably, the compounds are obtained by the following methods according to the invention which are described in more detail hereinafter.

a) In order to prepare compounds of general formula I wherein $R^1$ is as hereinbefore defined, but does not denote a hydrogen atom:

reacting a compound of general formula

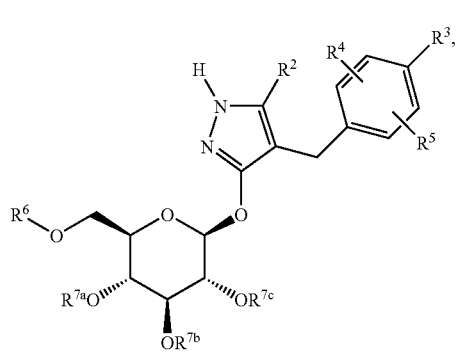

(II)

wherein $R^2$ to $R^6$ as well as $R^{7a}$, $R^{7b}$, $R^{7c}$ are as hereinbefore defined, with a compound of general formula $$Z^1\text{—}R^{1'} \qquad (III),$$

wherein $R^{1'}$ has the meanings given for $R^1$ hereinbefore, but does not denote a hydrogen atom, and $Z^1$ denotes a leaving group, preferably a halogen atom, for example a chlorine or bromine atom, a sulphonyloxy group, for example a methanesulphonyloxy or p-toluenesulphonyloxy group or a hydroxy group.

The reaction is conveniently carried out in a solvent, such as for example acetonitrile, toluene, tetrahydrofuran, dioxane, dimethylformamide, dimethylsulphoxide or N-methylpyrrolidinone, optionally in the presence of a base, such as for example potassium carbonate, caesium carbonate, sodium hydride or potassium-tert.-butoxide, at temperatures between 20° C. and 160° C.

With a compound of general formula III, wherein $Z^1$ denotes a hydroxy group, the reaction is carried out in the presence of a dehydrating agent, preferably in the presence of a phosphine and an azodicarboxylic acid derivative such as e.g. triphenylphosphine/diethyl azodicarboxylate, conveniently in a solvent such as methylene chloride, acetonitrile, tetrahydrofuran, dioxane, toluene or ethyleneglycoldiethylether or mixtures thereof at temperatures between −50 and 150° C., but preferably at temperatures between −20 and 80° C.

b) In order to prepare compounds of general formula I wherein $R^3$ denotes optionally substituted $C_{1-6}$-alkoxy, $C_{3-6}$-cycloalkyl-oxy, $C_{3-5}$-cycloalkyl-$C_{1-3}$-alkoxy or a meaning selected from the group A, which is as hereinbefore defined:

reacting a compound of general formula

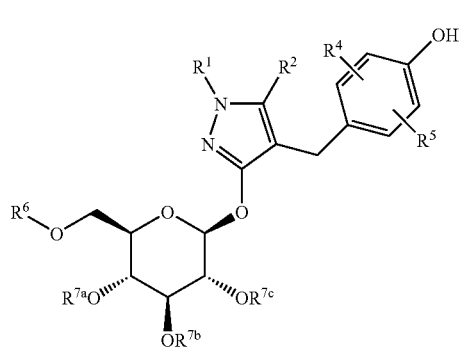

(IV)

wherein $R^1$, $R^2$ and $R^4$ to $R^6$ and $R^{7a}$, $R^{7b}$, $R^{7c}$ are as hereinbefore defined, with a compound of general formula $$Z^2\text{—}R^{3'} \qquad (V),$$

wherein $R^{3'}$ denotes optionally substituted $C_{1-6}$-alkoxy, $C_{3-6}$-cycloalkyl-oxy, $C_{3-5}$-cycloalkyl-$C_{1-3}$-alkoxy or a meaning selected from the group A, which is as hereinbefore defined, and $Z^2$ denotes a leaving group, preferably a halogen atom, for example a chlorine or bromine atom, a sulphonyloxy group, for example a methanesulphonyloxy or p-toluenesulphonyloxy group or a hydroxy group.

The reaction is conveniently carried out in a solvent, such as for example acetonitrile, toluene, tetrahydrofuran, dioxane, dimethylformamide, dimethylsulphoxide or N-methylpyrrolidinone, optionally in the presence of a base, such as for example potassium carbonate, caesium carbonate, sodium hydride or potassium-tert.-butoxide, at temperatures between 20° C. and 160° C.

With a compound of general formula V, wherein $Z^2$ denotes a hydroxy group, the reaction is carried out in the presence of a dehydrating agent, preferably in the presence of a phosphine and an azodicarboxylic acid derivative such as e.g. triphenylphosphine/diethyl azodicarboxylate, conveniently in a solvent such as methylene chloride, acetonitrile, tetrahydrofuran, dioxane, toluene or ethyleneglycoldiethylether or mixtures thereof at temperatures between –50 and 150° C., but preferably at temperatures between –20 and 80° C.

If according to the invention a compound of general formula I is obtained wherein $R^6$ denotes a hydrogen atom, this may be converted by acylation, for example by acylation in the presence of a base such as pyridine, collidine, triethylamine or N-ethyl-diisopropylamine, into a compound wherein $R^6$ denotes a ($C_{1-18}$-alkyl)carbonyl group, a ($C_{1-18}$-alkyl)oxycarbonyl group, an arylcarbonyl group or an aryl-($C_{1-3}$-alkyl)-carbonyl group. Suitable acylating agents may be, in particular, the corresponding activated acyl derivatives such as acid chlorides or anhydrides.

In the reactions described hereinbefore, any reactive groups present such as hydroxy, amino, alkylamino or imino groups may be protected during the reaction by conventional protecting groups which are cleaved again after the reaction.

For example, a protecting group for a hydroxy group may be a trimethylsilyl, acetyl, benzyl or tetrahydropyranyl group, protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran or methanol at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

The compounds of general formulae II to V used as starting materials are partly known from the literature or may be obtained by methods known from the literature (see Examples I to VI), optionally with the additional inclusion of protecting groups.

The compounds according to the invention may advantageously also be obtained by the methods described in the following examples, which may also be combined with methods known to the skilled artisan from the literature, for example, particularly the methods described in WO 02/36602, WO 02/088157, WO 01/16147, WO 02/053573, WO 02/068439, WO 02/068440 and WO 02/098893.

As already mentioned, the compounds of general formula I according to the invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-hSGLT2 or HEK-hSGLT2). These cell lines transport $^{14}$C-labelled alpha-methyl-glucopyranoside (14C-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 μg/ml zeocin (Invitrogen), and HEK293-hSGLT2 cells are cultivated in DMEM medium with 10% foetal calf serum and 250 μg/ml zeocin (Invitrogen).

The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 μl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 μg/ml of gentamycin). Two hundred-fifty microliters of assay buffer and 5 μl of test compound are then added to each well and the plate is incubated for a further 15 minutes in the incubator. Five microliters of 10% DMSO are used as the negative control. The reaction is started by adding 5 μl of $^{14}$C-AMG (0.05 μCi) to each well. After 2 hours' incubation at 37° C., 5% $CO_2$, the cells are washed again with 250 μl of PBS (20° C.) and then lysed by the addition of 25 μl of 0.1 N NaOH (5 min. at 37° C.). Two hundred microliters of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

Alternatively, measurement of the cellular membrane potential for hSGLT1 and hSGLT2 may also be used for the biological testing of substances. The cell model described earlier may be used for this. For the test, 10,000 cells per well of a black 384-well plate with a transparent base coated with poly-D-lysine are seeded in culture medium and incubated for 16 hours at 37° C., 5% $CO_2$. Then the cells are washed twice with glucose-free HBSS buffer (12.67 mol/l $CaCl_2$, 4.93 mmol/l $MgCl_2$, 4.07 mmol/l $MgSO_4$, 4.41 mmol/l $KH_2PO_4$; pH 7.4) and covered with 20 μl HBSS. After the addition of 20 μl of charging buffer (Membrane Potential Assay Kit Explorer R8126, Molecular Devices GmbH, Ismaning) and 20 μl of the substance to be tested in a suitable concentration, incubation is continued for a further 30 min. at 37° C., 5% $CO_2$. The measurement is carried out in the Fluorescent Imaging Plate Reader (Molecular Devices GmbH, Ismaning) at an excitation wavelength of 485 nm and is started by the addition of 20 μl of stimulant buffer (140 mM NaCl and 120 mM glucose). The depolarisation of the cell caused by the glucose-induced influx of $Na^+$ may be measured and quantified as a change in fluorescence.

The compounds of general formula I according to the invention may for example have EC50 values below 1000 nM, particularly below 200 nM, particularly preferably below 50 nM. For example, compound (4) of Example 3 has an EC50 value of about 5 nM in the SGLT-2 assay.

In view of their ability to inhibit the SGLT activity, the compounds of general formula I according to the invention and the corresponding pharmaceutically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

The patient whose illness or condition is to be treated or prevented according to the invention is a mammal, particularly a human being.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamid, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrat, fenofibrat), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-increasing compounds such as CETP inhibitors or ABC1 regulators or active substances for treating obesity, such as sibutramin or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

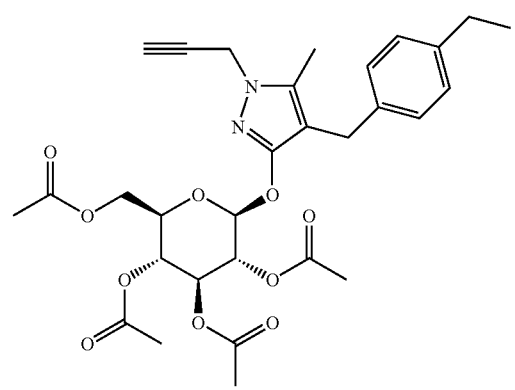

1-(2-propyn-1-yl)-3-(2,3,4,6-tetra-O-acetyl-β-D-glucopyranosyloxy)-4-(4-ethylbenzyl)-5-methyl-1H-pyrazole Six hundred milligrams of 3-(2,3,4,6-tetra-O-acetyl-β-D-glucopyranosyloxy)-4-(4-ethylbenzyl)-5-methyl-1H-pyrazole (for synthesis thereof cf. also WO 01/16147, WO 02/53573, WO 02/68439), 390 mg caesium carbonate and 0.091 ml propargyl bromide are stirred in 5 ml of dimethylformamide for 16 hours. A further 195 mg caesium carbonate and 0.046 ml propargyl bromide are added and the mixture is stirred for a further 3 hours at ambient temperature. The reaction mixture is distributed between 25 ml of water and 30 ml of ethyl acetate. The organic phase is separated off, dried and evaporated down. The residue is purified by chromatography through a silica gel column with a methylene chloride/methanol gradient (99:1 to 95:5).

Yield: 234 mg (36% of theory)

Rf value: 0.65 (silica gel; methylene chloride/methanol=15:1)

Mass spectrum (ESI+): m/z=585 [M+H]+

The following compounds are obtained analogously to Example I:

(1) 1-(2-butyn-1-yl)-3-(2,3,4,6-tetra-O-acetyl-β-D-glucopyranosyloxy)-4-(4-ethylbenzyl)-5-methyl-1H-pyrazole

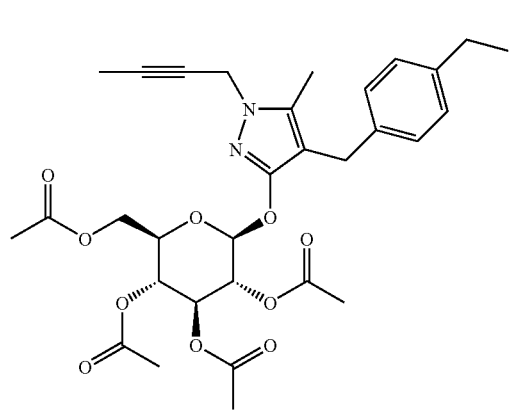

$R_f$ value: 0.58 (silica gel, methylene chloride/methanol/cyclohexane=20:1:2)

Mass spectrum (ESI+): m/z=599 [M+H]+

(2) 1-isopropyl-3-(2,3,4,6-tetra-O-acetyl-β-D-glucopyranosyloxy)-4-(4-benzyloxybenzyl)-5-methyl-1H-pyrazole

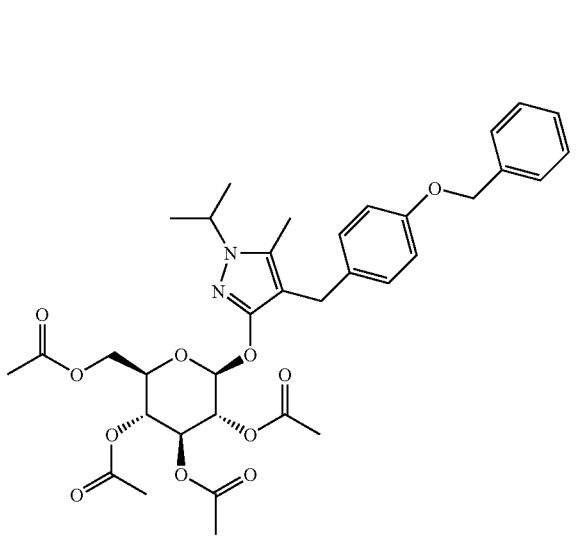

prepared from the compound of Example IV by reaction with isopropyl iodide $R_f$ value: 0.72 (silica gel, cyclohexane/ethyl acetate=1:1)

Mass spectrum (ESI+): m/z=667 [M+H]+

In addition partially deacetylated derivatives of the title compound with $R_f$ values of 0.48, 0.33 and 0.22 are isolated from the reaction mixture (silica gel, cyclohexane/ethyl acetate=1:1).

EXAMPLE II

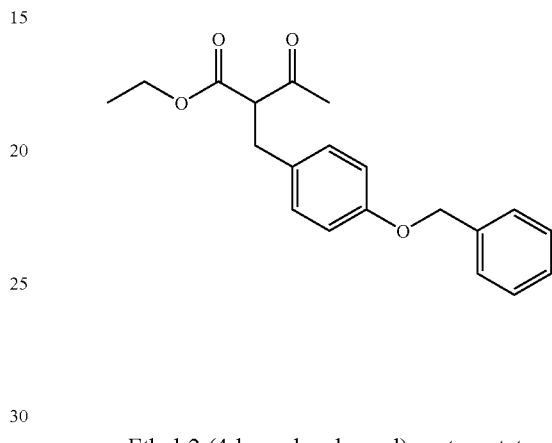

Ethyl 2-(4-benzyloxybenzyl)-acetoacetate

Prepared by treating ethyl acetoacetate with sodium hydride and subsequently reacting with 4-benzyloxybenzyl-bromide. The reaction is carried out in tetrahydrofuran.

$R_f$ value: 0.48 (silica gel, cyclohexane/ethyl acetate=4:1)

Mass spectrum (ESI+): m/z=344 [M+NH4]+

EXAMPLE III

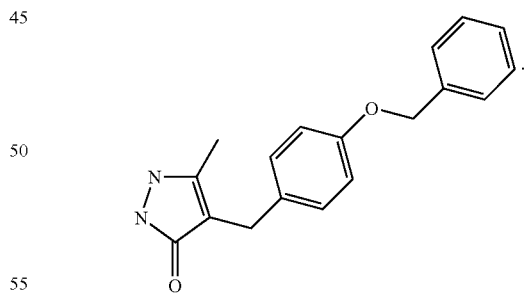

1,2-dihydro-4-(4-benzyloxybenzyl)-5-methyl-pyrazol-3-one

Prepared from the compound of Example II by reacting with hydrazine hydrate in ethanol $R_f$ value: 0.35 (silica gel, methylene chloride/methanol=9:1)

Mass spectrum (ESI−): m/z=293 [M−H]−

EXAMPLE IV

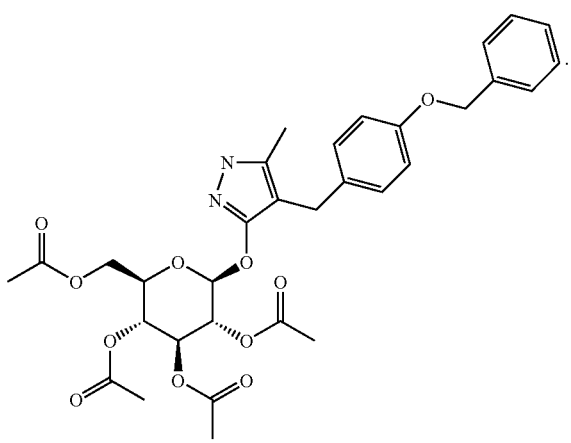

3-(2,3,4,6-Tetra-O-acetyl-β-D-glucopyranosyloxy)-4-(4-benzyloxybenzyl)-5-methyl-1H-pyrazole 5.1 g of 1,2-dihydro-4-(4-benzyloxybenzyl)-5-methyl-pyrazol-3-one, 7.13 g of 2,3,4,6-tetra-O-acetyl-alpha-glucopyranosylbromide and 4.78 g of silver carbonate are stirred for 3 days at 65° C. with the exclusion of light. The reaction mixture is filtered through a suction filter, the solid residue is washed with methylene chloride and the filtrate is evaporated down. The crude product is purified by chromatography through a silica gel column with an ethyl acetate/cyclohexane gradient (1:1 to 3:1).

Yield: 4.7 g (43% of theory)
Rf value: 0.45 (silica gel; ethyl acetate/cyclohexane=3:1)
Mass spectrum (ESI$^+$): m/z=625 [M+H]$^+$

EXAMPLE V

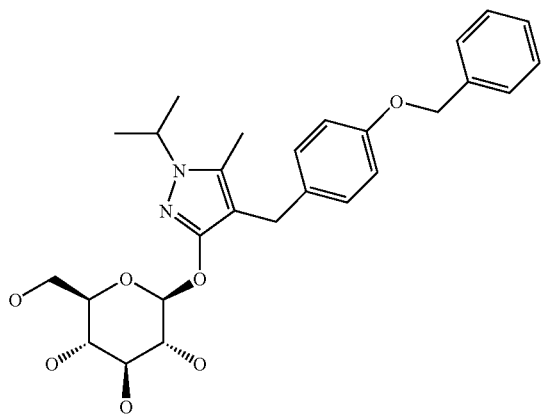

1-isopropyl-3-(β-D-glucopyranosyloxy)-4-(4-benzyloxybenzyl)-5-methyl-1H-pyrazole Prepared from the partially deacetylated derivatives of the compound of Example I(2) by treatment with lithium hydroxide in tetrahydrofuran/methanol.

Rf value: 0.10 (silica gel; methylene chloride/methanol=9:1)
Mass spectrum (ESI$^+$): m/z=499 [M+H]$^+$

EXAMPLE VI

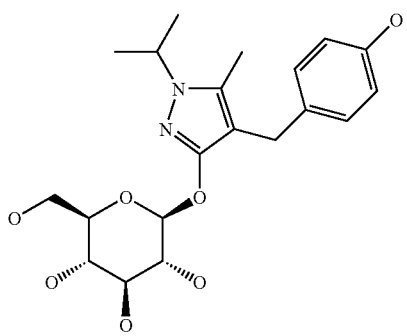

1-isopropyl-3-(β-D-glucopyranosyloxy)-4-(4-hydroxybenzyl)-5-methyl-1H-pyrazole

Prepared by catalytic hydrogenation of 1-isopropyl-3-(β-D-glucopyranosyloxy)-4-(4-benzyloxybenzyl)-5-methyl-1H-pyrazole in methanol in the presence of palladium on activated charcoal (10% Pd) at ambient temperature (approx. 20° C.)

Rf value: 0.36 (silica gel; methylene chloride/methanol=6:1)
Mass spectrum (ESI$^+$): m/z=409 [M+H]$^+$ The following compound is obtained analogously to Example VI:

(1) 1-isopropyl-3-(2,3,4,6-tetra-O-acetyl-β-D-glucopyranosyloxy)-4-(4-hydroxybenzyl)-5-methyl-1H-pyrazole

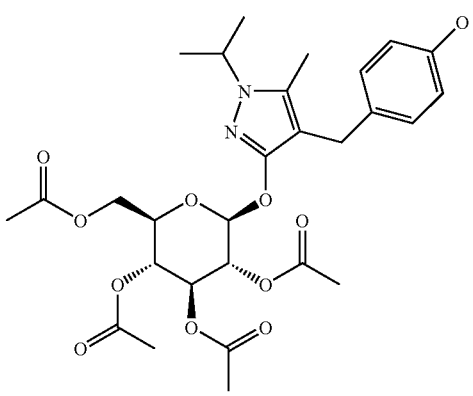

Rf value: 0.30 (silica gel; methylene chloride/methanol=9:1)

Preparation of the Final Compounds:

EXAMPLE 1

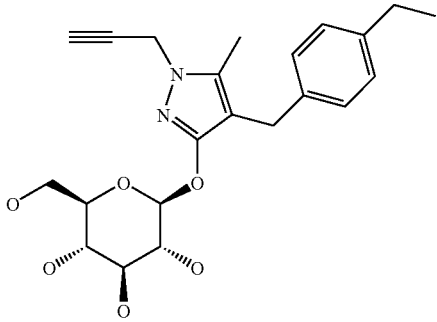

1-(2-propyn-1-yl)-3-(β-D-glucopyranosyloxy)-4-(4-ethylbenzyl)-5-methyl-1H-pyrazole A solution of 250 mg of 1-(2-propyn-1-yl)-3-(2,3,4,6-tetra-O-acetyl-β-D-glucopyranosyloxy)-4-(4-ethylbenzyl)-5-methyl-1H-pyrazole in a mixture of 1 ml of methanol and 2 ml of tetrahydrofuran is cooled in the ice bath and combined with 1.81 ml of a 1 M aqueous lithium hydroxide solution and stirred for 2 hours. The reaction mixture is combined with 5 ml of water and 5 ml of saturated saline solution and extracted with ethyl acetate. The organic phase is separated off, washed with saturated saline solution, dried and evaporated down.

Yield: 167 mg (93% of theory)

Rf value: 0.17 (silica gel; methylene chloride/methanol=9:1)

Mass spectrum (ESI+): m/z=417 [M+H]+

The following compound is obtained analogously to Example 1:

(1) 1-(2-butyn-1-yl)-3-(β-D-glucopyranosyloxy)-4-(4-ethylbenzyl)-5-methyl-1H-pyrazole

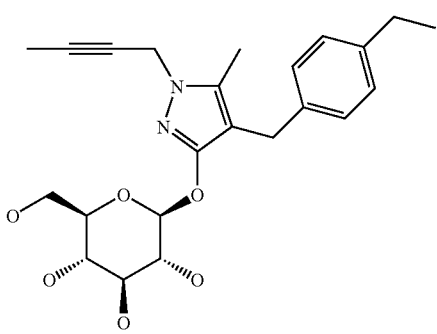

R$_f$ value: 0.40 (silica gel, methylene chloride/methanol=9:1)

Mass spectrum (ESI+): m/z=431 [M+H]+

EXAMPLE 2

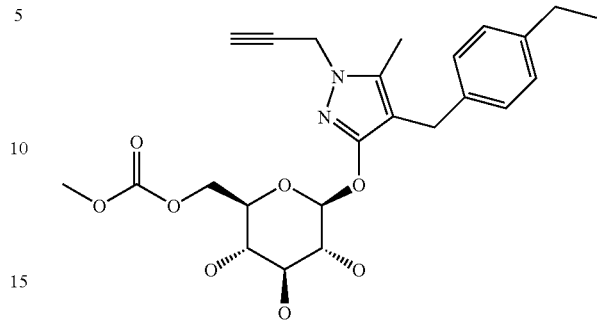

1-(2-propyn-1-yl)-3-(6-O-methoxycarbonyl-β-D-glucopyranosyloxy)-4-(4-ethylbenzyl)-5-methyl-1H-pyrazole One hundred milligrams of 1-(2-propyn-1-yl)-3-(β-D-glucopyranosyloxy)-4-(4-ethylbenzyl)-5-methyl-1H-pyrazole in 0.5 ml 2,4,6-collidine are combined with 0.023 ml of methyl chloroformate in the ice bath and stirred for 6 hours. 3.5 ml 0.1 N hydrochloric acid are added to the reaction mixture and this is then extracted with 10 ml of ethyl acetate. The organic phase is separated off, washed with saturated saline solution and evaporated down. The residue is taken up in 20 ml of ethyl acetate, washed again with 5 ml 0.1 N hydrochloric acid and saturated saline solution, dried and evaporated down.

Yield: 85 mg (75% of theory)

R$_f$ value: 0.30 (silica gel; methylene chloride/methanol=9:1)

Mass spectrum (ESI+): m/z=475 [M+H]+

The following compound is obtained analogously to Example 2:

(2) 1-(tetrahydropyran-4-yl)-3-(6-O-ethoxycarbonyl-β-D-glucopyranosyloxy)-4-(4-methoxybenzyl)-5-methyl-1H-pyrazole

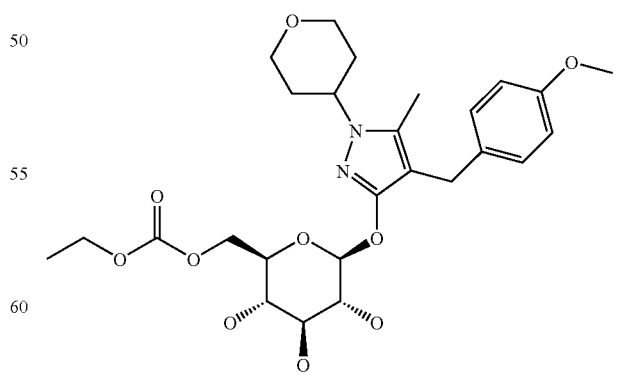

R$_f$ value: 0.35 (silica gel; methylene chloride/methanol=9:1)

Mass spectrum (ESI+): m/z=537 [M+H]+

EXAMPLE 3

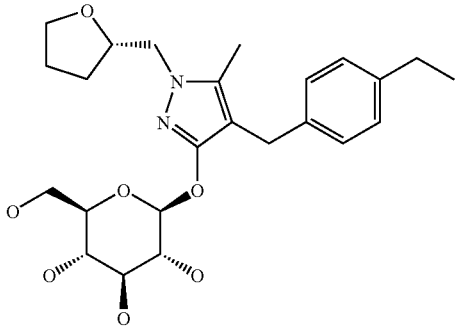

1-((S)-tetrahydrofuran-2-ylmethyl)-3-(β-D-glucopy-
ranosyloxy)-4-(4-ethylbenzyl)-5-methyl-1H-pyra-
zole Three hundred milligrams of 3-(2,3,4,6-Tetra-O-acetyl-β-D-glucopyranosyloxy)-4-(4-ethylbenzyl)-5-methyl-1H-pyrazole (for its synthesis cf. also WO 01/16147, WO 02/53573, WO 02/68439), 1808 mg caesium carbonate and 666 mg of (tetrahydrofuran-2-ylmethyl) (S)-p-toluene-sulphonate are stirred in 5 ml of dimethylformamide for 5 hours at 100° C. The reaction mixture is evaporated down, and the residue is combined with 0.9 ml of methanol, 1.8 ml of tetrahydrofuran and 1.5 ml of 1 N aqueous lithium hydroxide solution while being cooled in the ice bath. After 2 hours' stirring the reaction mixture is distributed between 20 ml of water and 30 ml of ethyl acetate. The organic phase is washed with saturated saline solution, dried and evaporated down. The residue is purified by chromatography through a silica gel column with methylene chloride/methanol (9:1).

Yield: 128 mg (50% of theory)

Rf value: 0.40 (silica gel, methylene chloride/methanol=7:1)

Mass spectrum (ESI$^+$): m/z 463 [M+H]$^+$

The following compounds are obtained analogously to Example 3:

(3) 1-((S)-tetrahydrofuran-3-yl)-3-(β-D-glucopyra-
nosyloxy)-4-(4-ethylbenzyl)-5-methyl-1H-pyrazole

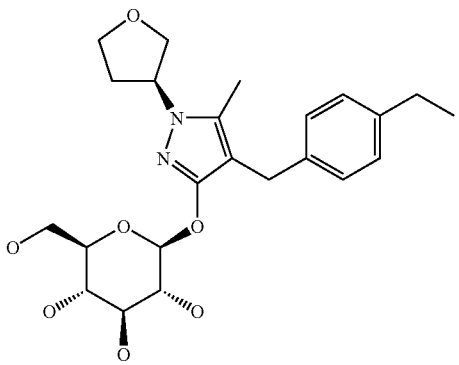

(Tetrahydrofuran-3-yl) (R)-p-toluenesulphonate may be used as alkylating agent.

R$_f$ value: 0.40 (silica gel, methylene chloride/methanol=7:1)

Mass spectrum (ESI$^+$): m/z=449 [M+H]$^+$ (4) 1-(tetrahydropyran-4-yl)-3-(β-D-glucopyranosy-
loxy)-4-(4-ethylbenzyl)-5-methyl-1H-pyrazole

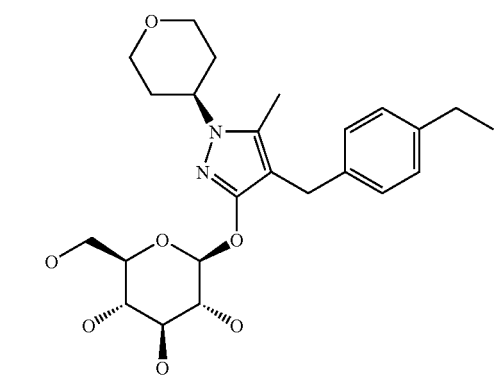

(Tetrahydropyran-4-yl) p-toluenesulphonate may be used as alkylating agent.

R$_f$ value: 0.40 (silica gel, methylene chloride/methanol=7:1)

Mass spectrum (ESI$^+$): m/z=463 [M+H]$^+$ (5) 1-(tetrahydropyran-4-yl)-3-(β-D-glucopyranosy-
loxy)-4-(4-methoxybenzyl)-5-methyl-1H-pyrazole

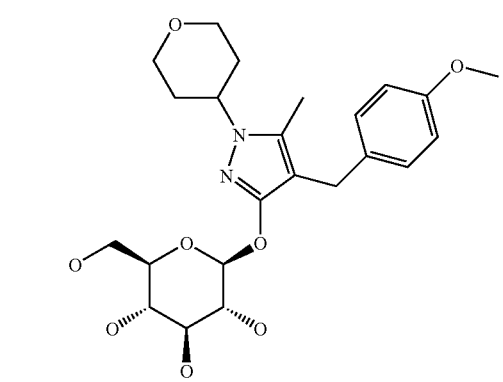

The starting material is for example 3-(2,3,4,6-tetra-O-acetyl-β-D-glucopyranosyloxy)-4-(4-methoxybenzyl)-5-methyl-1H-pyrazole, as described analogously in WO 01/16147 or WO 02/53573. (Tetrahydropyran-4-yl) p-toluenesulphonate may be used as alkylating agent.

R$_f$ value: 0.20 (silica gel, methylene chloride/methanol=9:1)

Mass spectrum (ESI$^+$): m/z=465 [M+H]$^+$

EXAMPLE 4

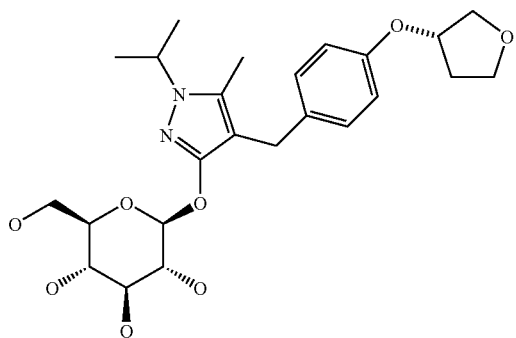

1-isopropyl-3-(β-D-glucopyranosyloxy)-4-[4-((S)-tetrahydrofuran-3-yloxy)benzyl]-5-methyl-1H-pyrazole Fifty milligrams of 1-isopropyl-3-(β-D-glucopyranosyloxy)-4-(4-hydroxybenzyl)-5-methyl-1H-pyrazole, 33.92 mg of (tetrahydrofuran-3-yl) (R)-p-toluenesulphonate and 45.61 mg of caesium carbonate are stirred in 0.5 ml of dimethylformamide at 50° C. for 16 hours. The reaction mixture is evaporated down and the residue is purified by chromatography through a silica gel column.

Yield: 35 mg (60% of theory)

$R_f$ value: 0.55 (silica gel, methylene chloride/methanol=6:1)

Mass spectrum (ESI$^+$): m/z=479 [M+H]$^+$

The following compounds are obtained analogously to Example 4:

(6) 1-isopropyl-3-(β-D-glucopyranosyloxy)-4-[4-((S)-tetrahydrofuran-2-yl-methyloxy)benzyl]-5-methyl-1H-pyrazole

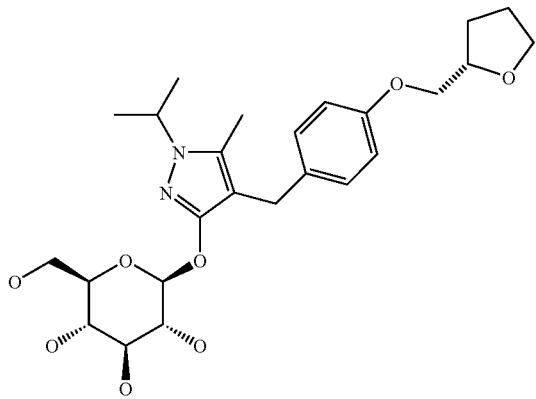

Rf value: 0.55 (silica gel, methylene chloride/methanol=6:1)

Mass spectrum (ESI$^+$): m/z=493 [M+H]$^+$ (7) 1-isopropyl-3-(β-D-glucopyranosyloxy)-4-[4-(tetrahydropyran-4-yloxy)benzyl]-5-methyl-1H-pyrazole

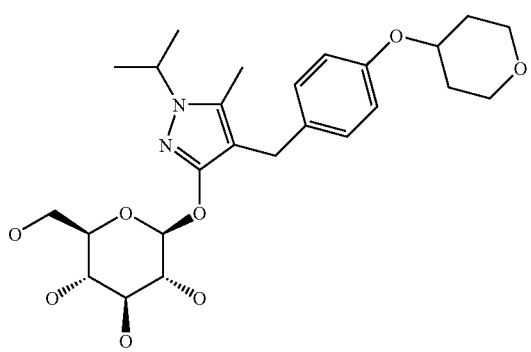

Rf value: 0.54 (silica gel, methylene chloride/methanol=6:1)

Mass spectrum (ESI$^+$): m/z=493 [M+H]$^+$ (8) 1-isopropyl-3-(β-D-glucopyranosyloxy)-4-[4-((R)-tetrahydrofuran-3-yloxy)benzyl]-5-methyl-1H-pyrazole

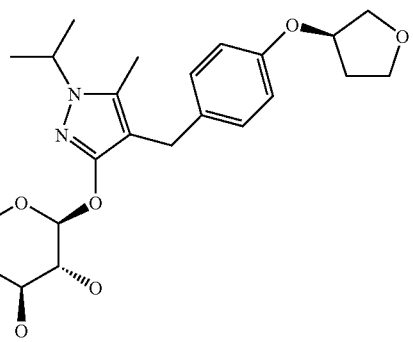

Prepared by alkylation of the compound of Example VI(1) and subsequent hydrolysis of the acetyl groups analogously to Example V Mass spectrum (ESI$^+$): m/z=479 [M+H]$^+$ The following compounds are also prepared analogously to the above-mentioned Examples and other methods known from the literature:

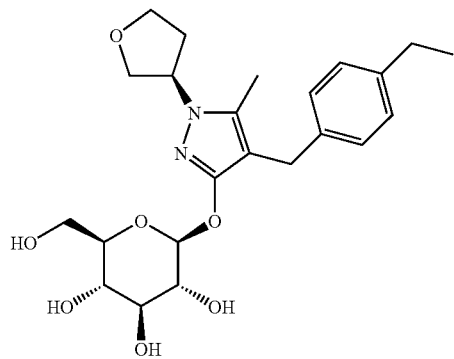
(10)
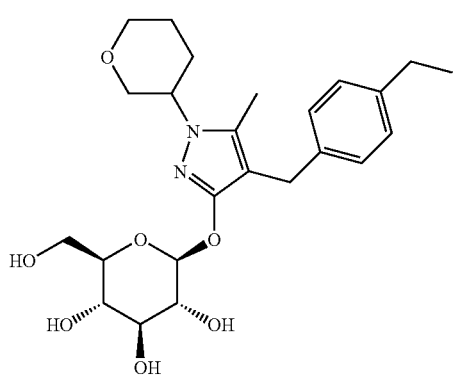
(11)
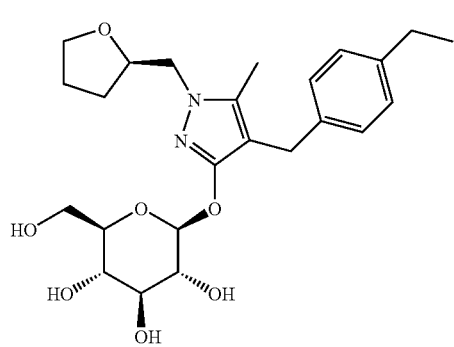
(12)
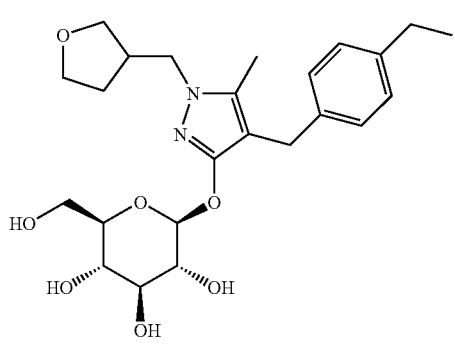
(13)
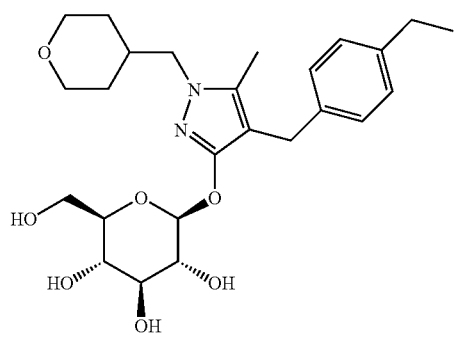
(14)
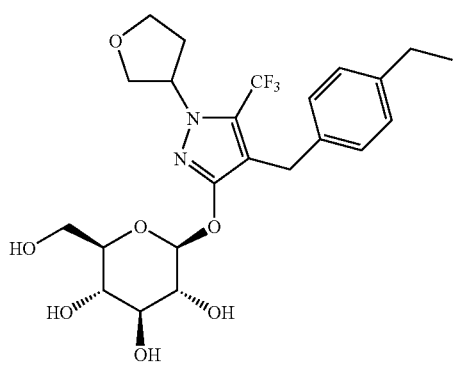
(15)
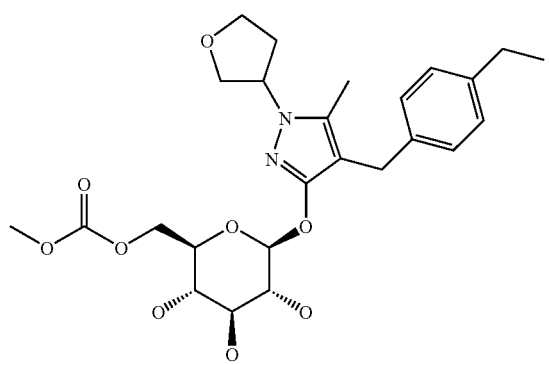
(16)
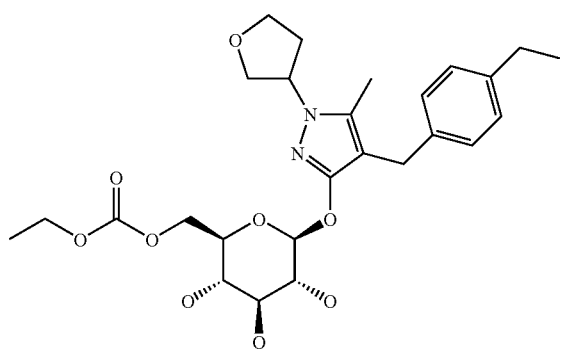
(17)

-continued
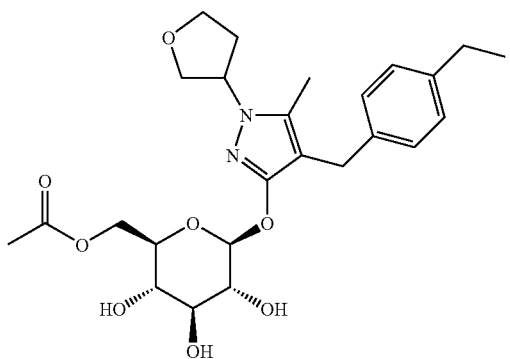
(18)
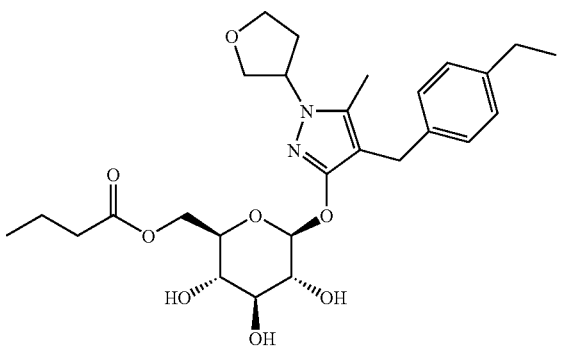
(19)
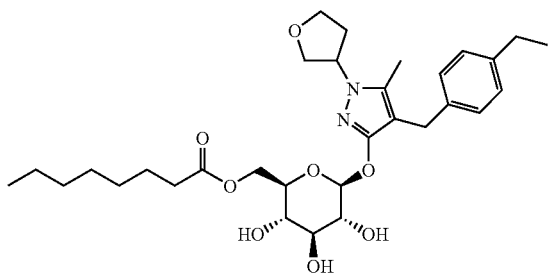
(20)
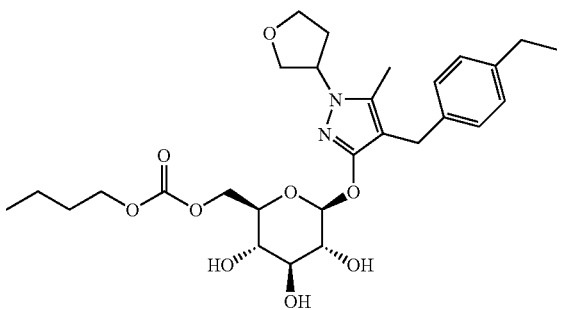
(21)
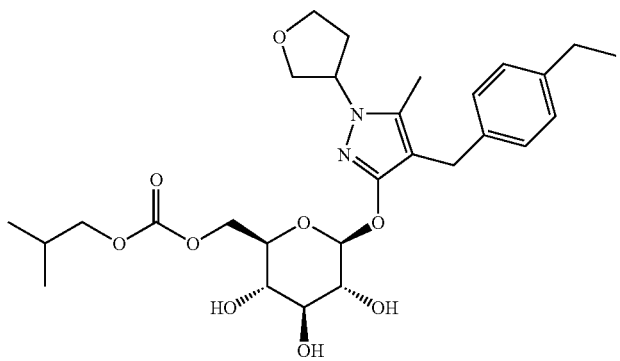
(22)
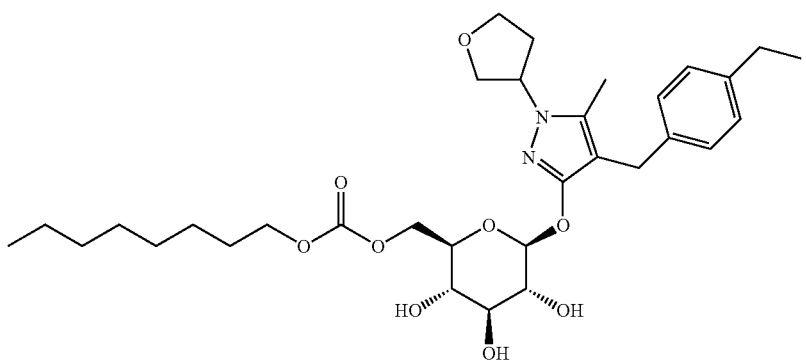
(23)

-continued
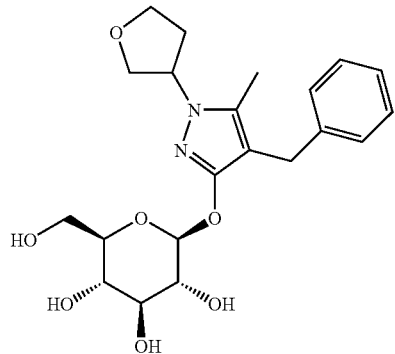
(24)
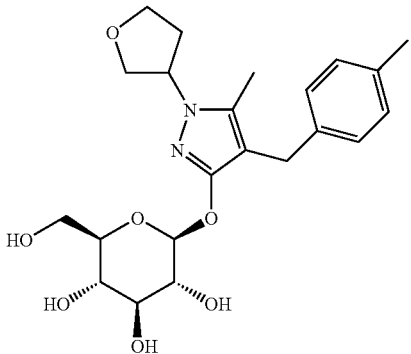
(25)
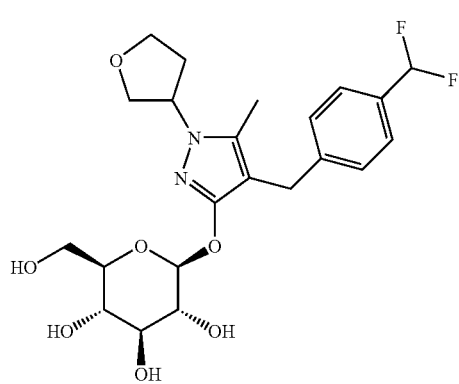
(26)
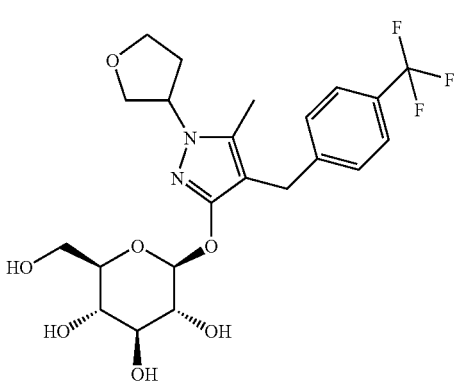
(27)
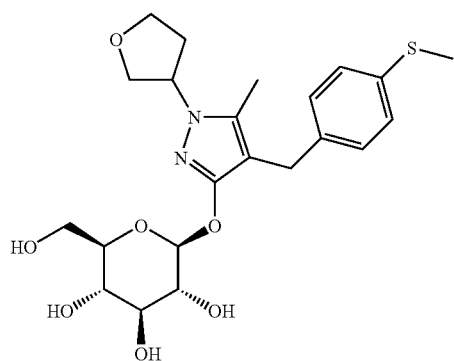
(28)
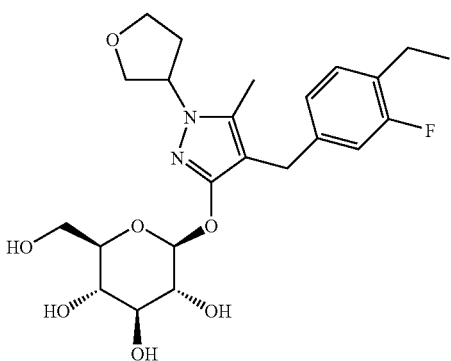
(29)
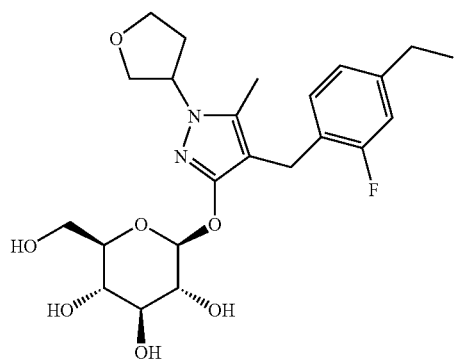
(30)
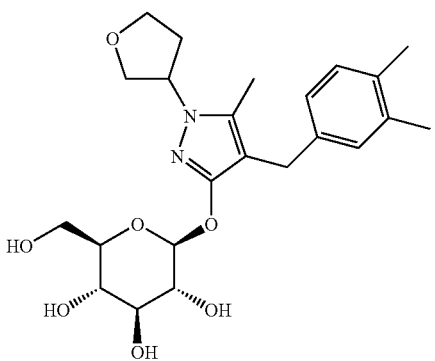
(31)

-continued
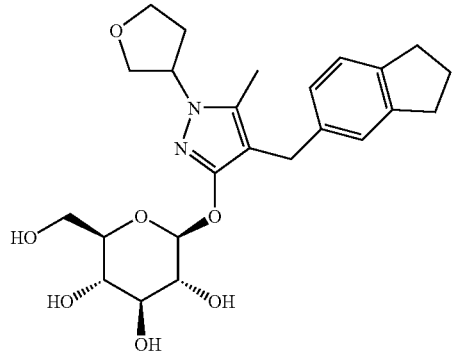
(32)
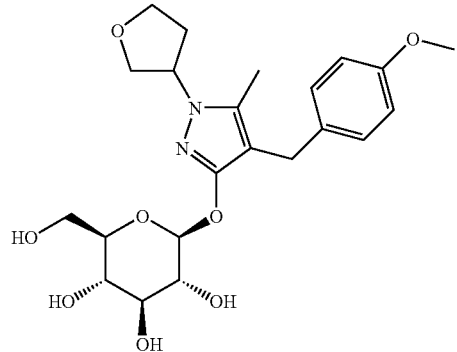
(33)
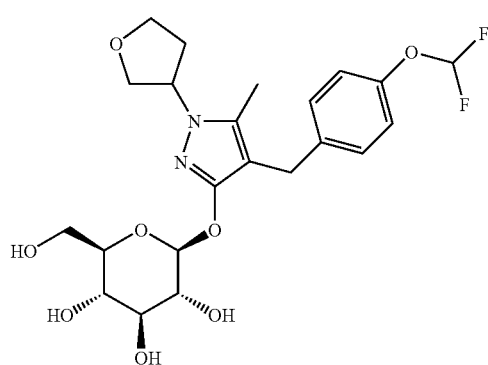
(34)
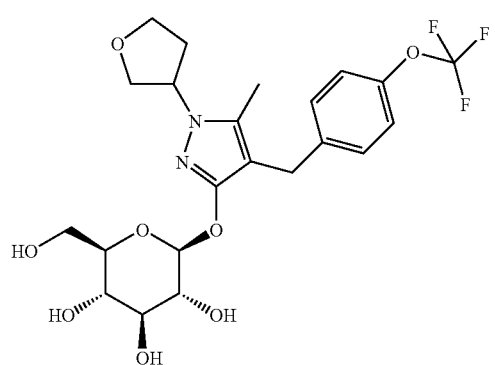
(35)
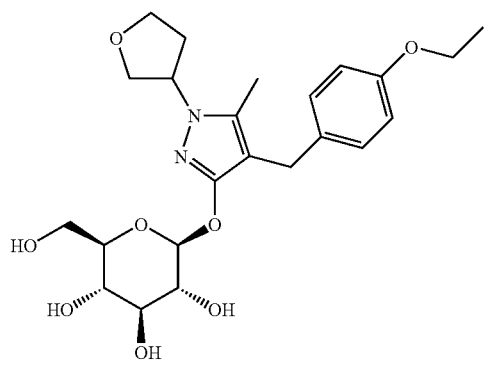
(36)
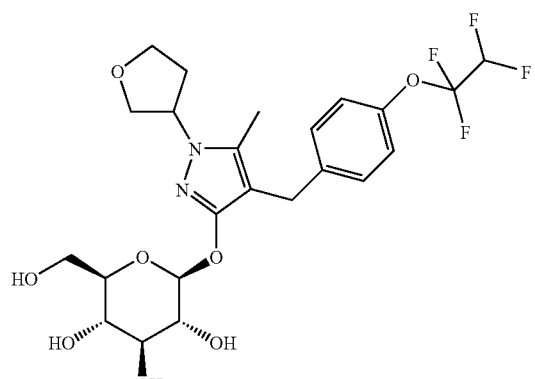
(37)
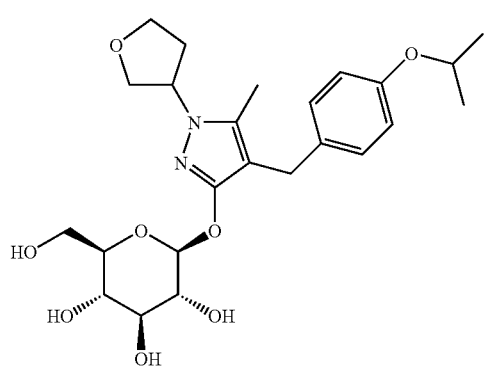
(38)
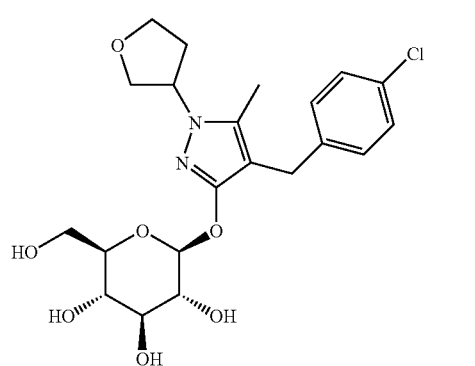
(39)

-continued
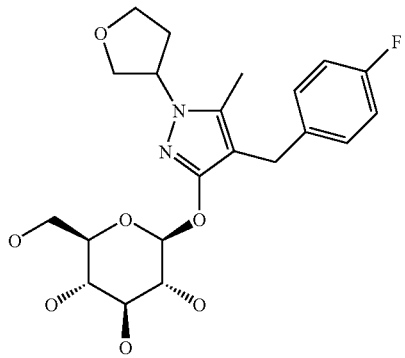 (40)
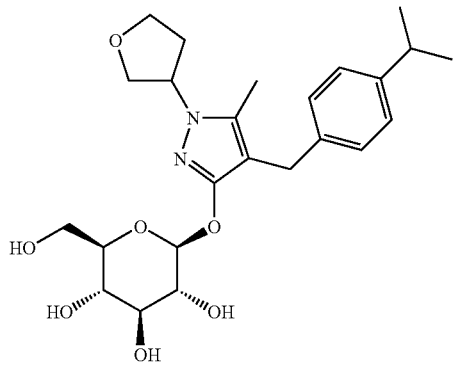 (41)
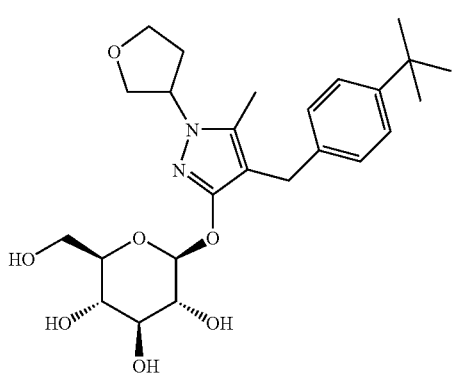 (42)
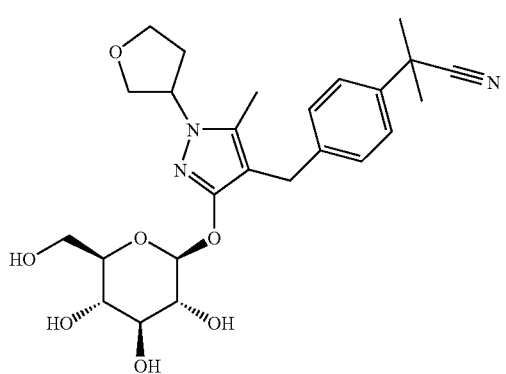 (43)
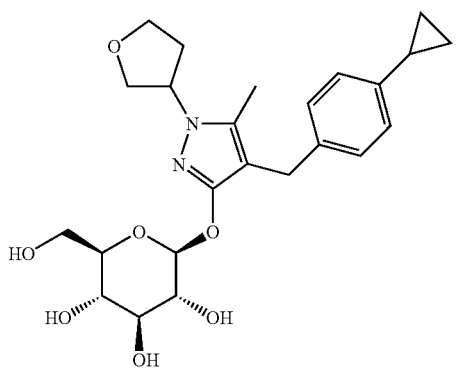 (44)
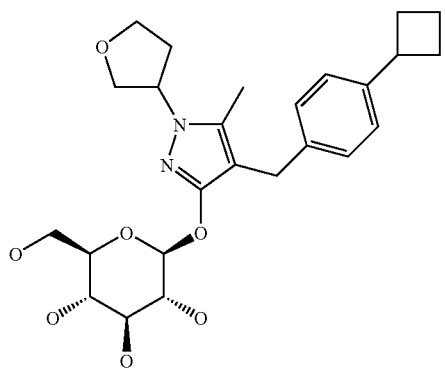 (45)
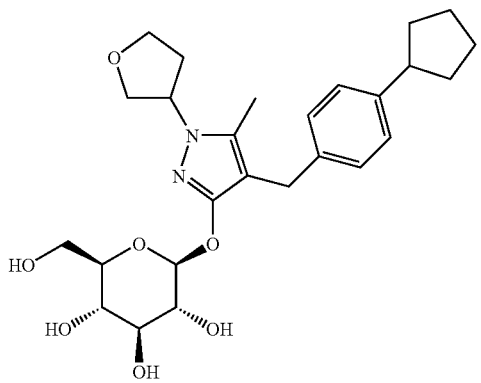 (46)
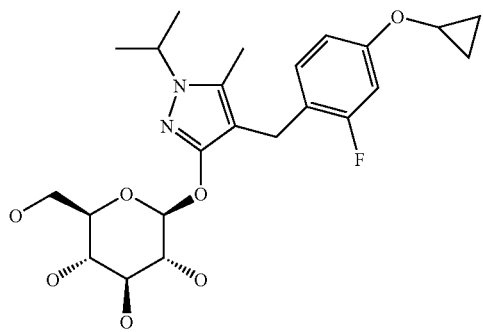 (47)

-continued
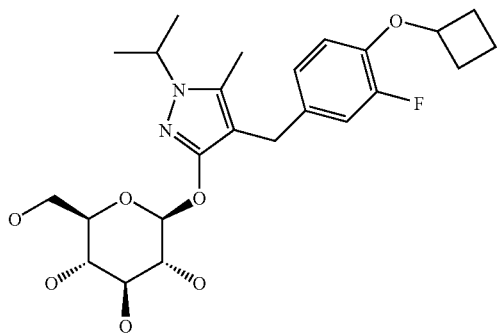 (48)
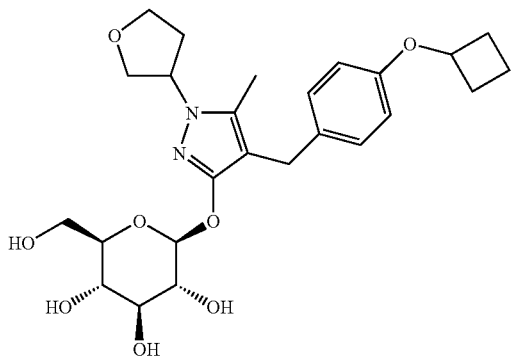 (49)
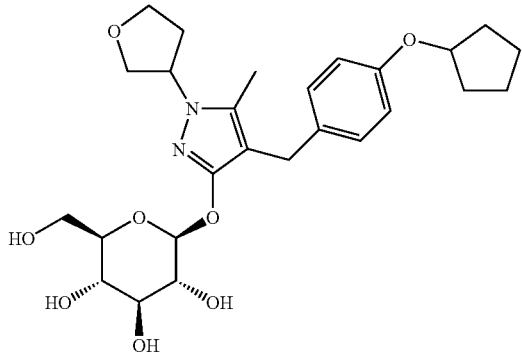 (50)
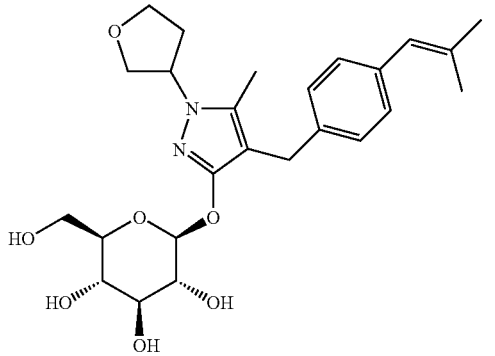 (51)
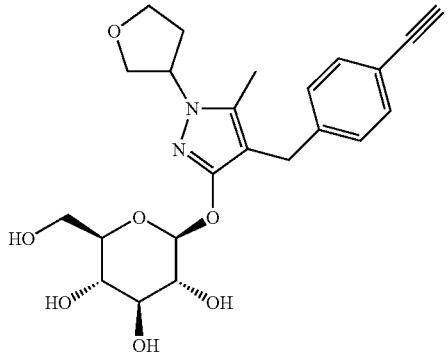 (52)
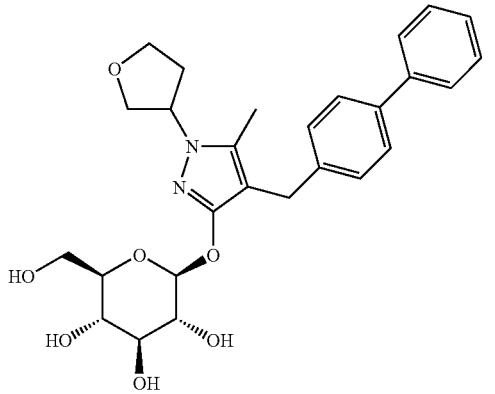 (53)
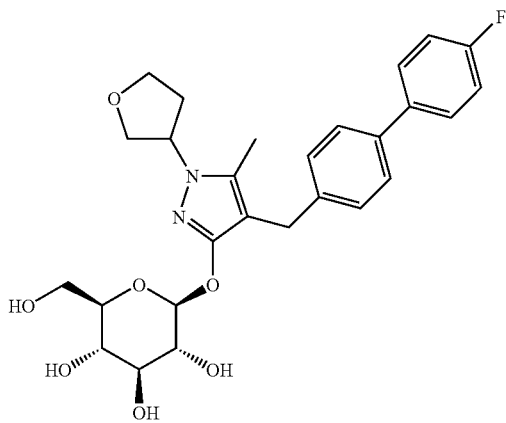 (54)
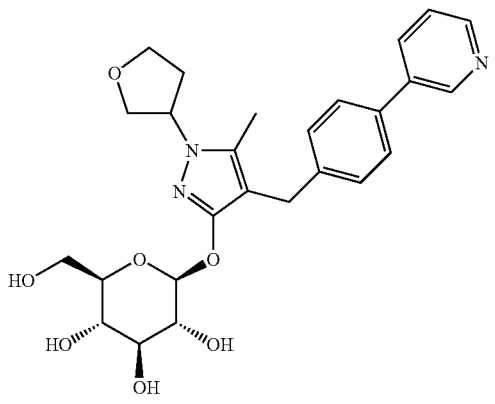 (55)

-continued
(56)
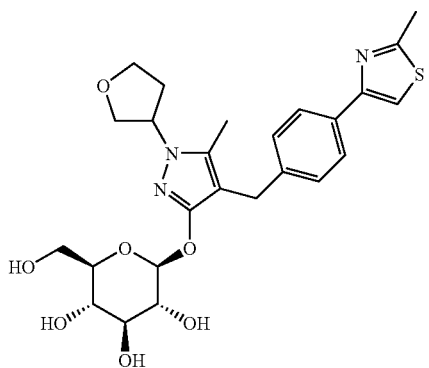
(57)
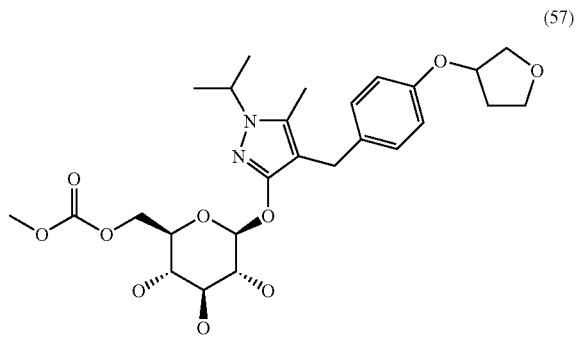
(58)
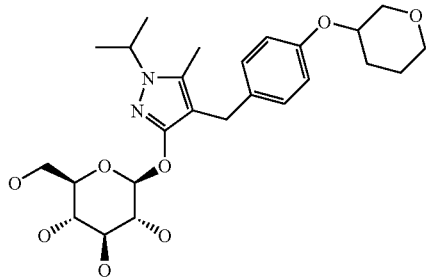
(59)
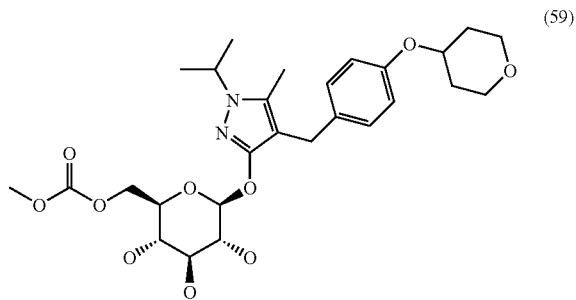
(60)
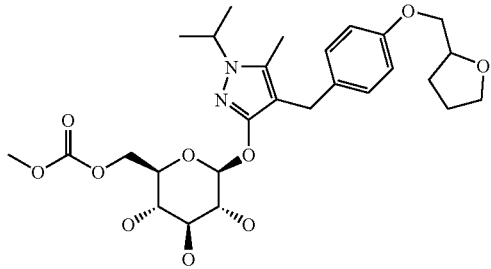
(61)
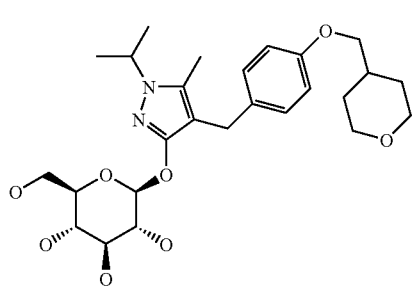
(62)
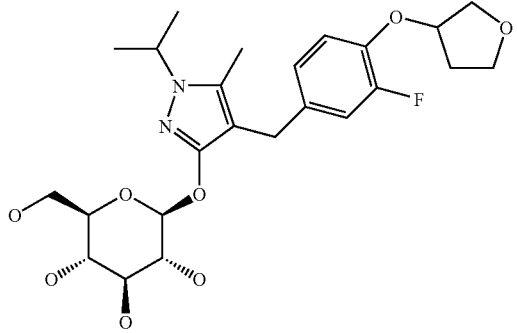
(63)
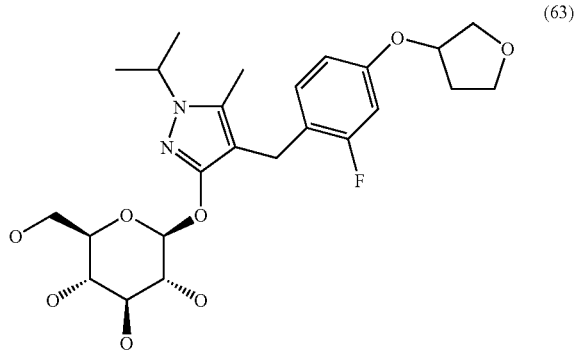

-continued
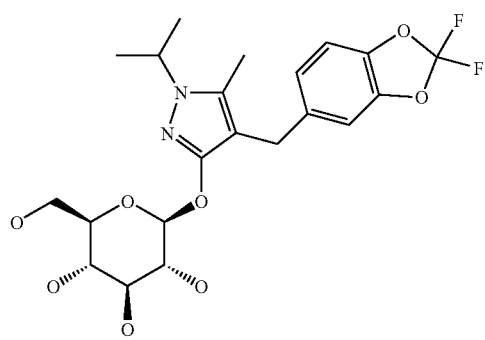
(64)
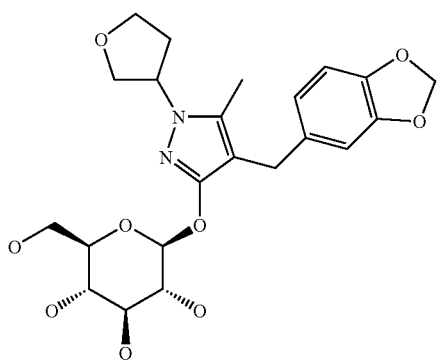
(65)
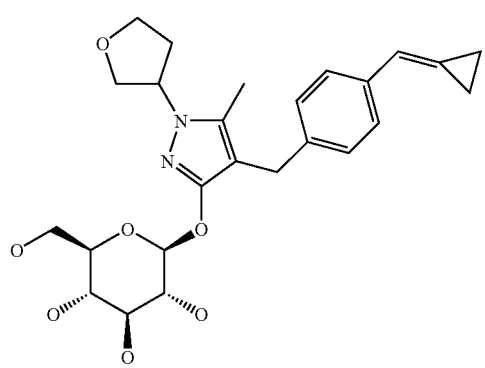
(66)
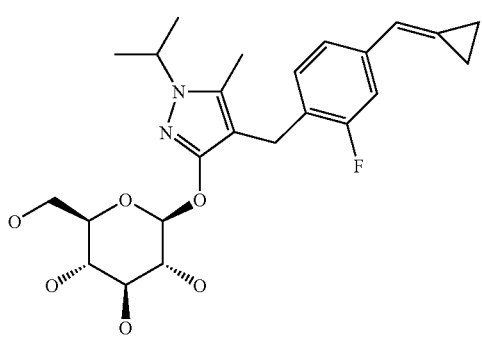
(67)
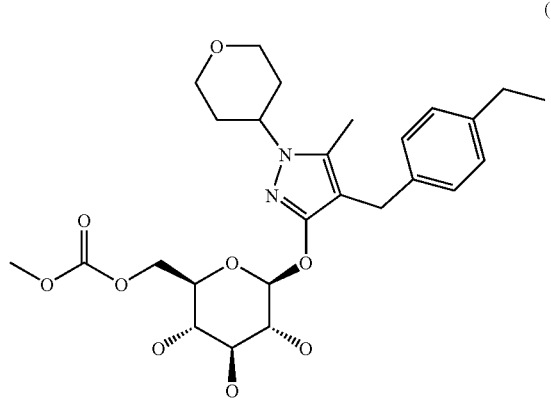
(68)
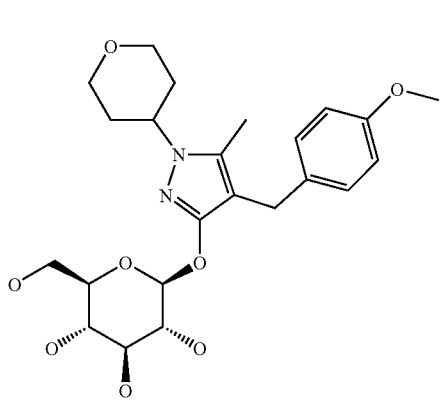
(69)
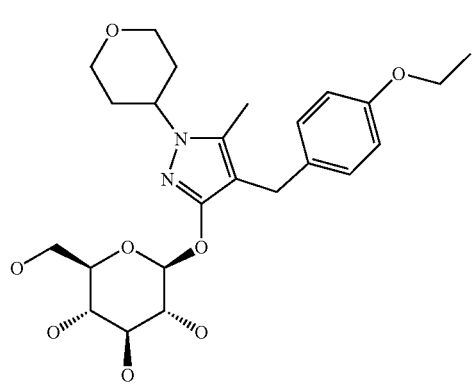
(70)
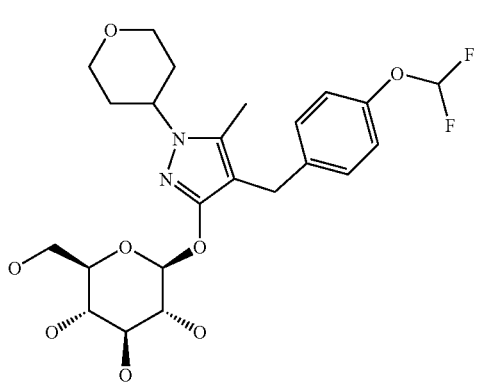
(71)

-continued
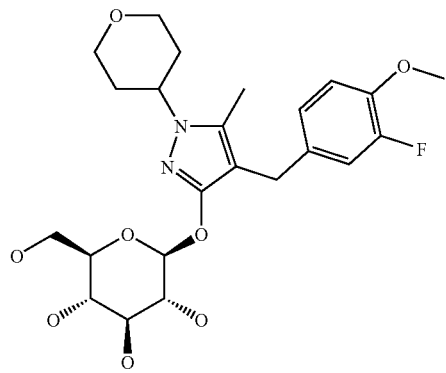
(72)
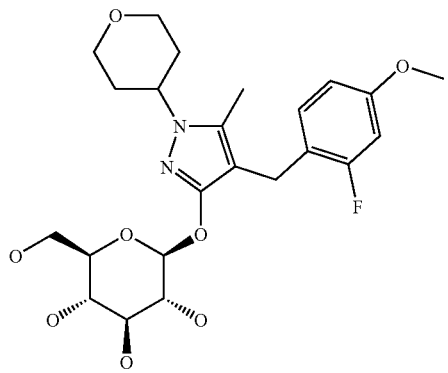
(73)
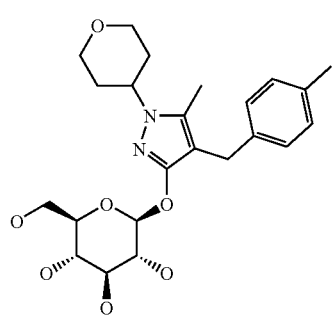
(74)
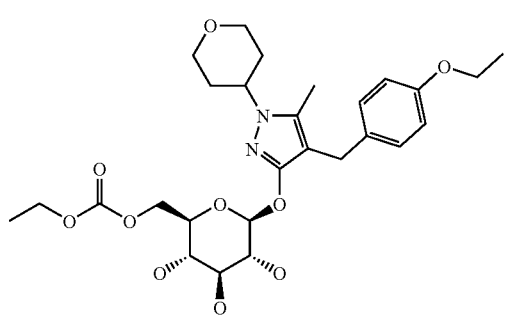
(75)
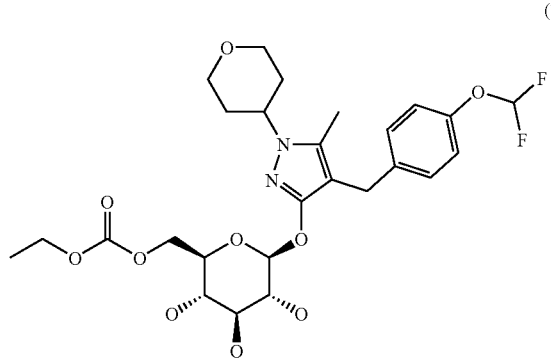
(76)
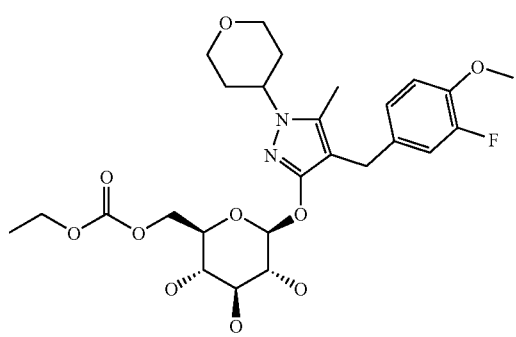
(77)
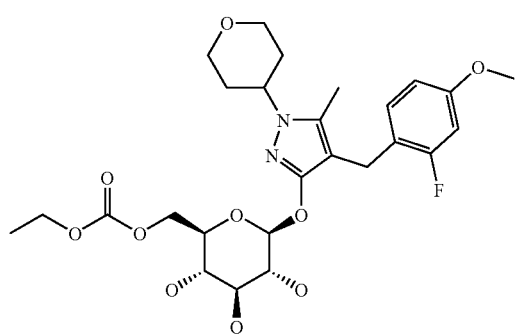
(78)
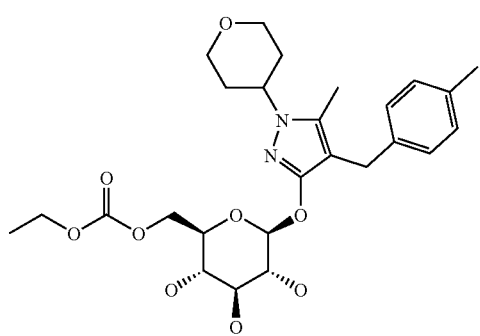
(79)

The following are examples of formulations in which the phrase "active substance" denotes one or more compounds according to the invention, including the salts thereof. In the case of one of the combinations with one or more other active substances the term "active substance" also includes the additional active substances.

EXAMPLE A

| Tablets containing 100 mg of active substance Composition: 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

| Tablets containing 150 mg of active substance Composition: 1 tablet contains: | |
| --- | --- |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| Weight of tablet: | 300 mg |
| --- | --- |
| die: | 10 mm, flat |

EXAMPLE C

| Hard gelatine capsules containing 150 mg of active substance 1 capsule contains: | | |
| --- | --- | --- |
| active substance | | 150.0 mg |
| corn starch (dried | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

| Suppositories containing 150 mg of active substance 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

| Ampoules containing 10 mg active substance Composition: | |
| --- | --- |
| active substance | 10.0 mg |
| 0.01 N hydrochloric acid q.s. | ad 2.0 ml |
| double-distilled water | |

Preparation:

The active substance is dissolved in the necessary amount of 0.01 N HCl, made isotonic with common salt, filtered sterile and transferred into 2 ml ampoules.

EXAMPLE F

| Ampoules containing 50 mg of active substance Composition: | |
| --- | --- |
| active substance | 50.0 mg |
| 0.01 N hydrochloric acid q.s. | ad 10.0 ml |
| double-distilled water | |

Preparation:

The active substance is dissolved in the necessary amount of 0.01 N HCl, made isotonic with common salt, filtered sterile and transferred into 10 ml ampoules.

What is claimed is:

1. A compound of formula (I):

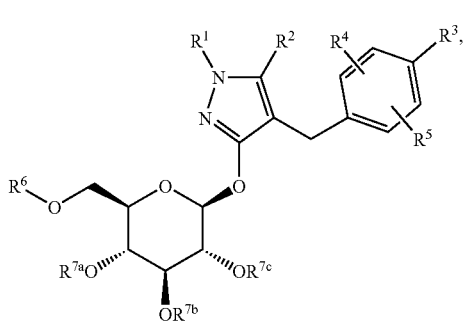

wherein

R$^1$ denotes C$_{3-6}$-alkynyl, tetrahydrofuran-3-yl, tetrahydropyran-3-yl, tetrahydropyran-4-yl, tetrahydrofuranyl-C$_{1-3}$-alkyl, tetrahydropyranyl-C$_{1-3}$-alkyl, pyrrolidin-3-yl, piperidin-3-yl, piperidin-4-yl, or a pyrrolidin-3-yl, piperidin-3-yl or piperidin-4-yl group, while in the latter three groups the nitrogen atom may be substituted by a C$_{1-4}$-alkyl, formyl, C$_{1-4}$-alkyl-carbonyl, C$_{1-4}$-alkylsulphonyl, cyano, aminocarbonyl, (C$_{1-4}$-alkyl)-aminocarbonyl, di-(C$_{1-4}$-alkyl)-aminocarbonyl or (C$_{1-4}$-alkyl)-oxycarbonyl group, or if R$^3$ (a) is selected from one of the definitions of the group A; or (b) together with R$^4$ denotes difluoromethylenedioxy; or (c) denotes C$_{3-6}$-cycloalkyl-oxy or C$_{3-6}$-cycloalkylidene-methyl and simultaneously R$^4$ denotes fluorine, chlorine, bromine, C$_{1-3}$-alkyl, C$_{1-3}$-alkoxy or a methyl or methoxy group substituted by 1 to 3 fluorine atoms;

then R$^1$ may also represent hydrogen, C$_{1-6}$-alkyl, a C$_{1-4}$-alkyl group substituted by 1 to 3 fluorine atoms, a C$_{2-4}$-alkyl group substituted by a hydroxy or C$_{1-3}$-alkoxy group, or C$_{3-6}$-alkenyl, C$_{3-6}$-cycloalkyl, C$_{3-6}$-cycloalkyl-C$_{1-3}$-alkyl, aryl or aryl-C$_{1-3}$-alkyl, and R$^2$ denotes C$_{1-4}$-alkyl, a C$_{1-4}$-alkyl group substituted by 1 to 3 fluorine atoms, or C$_{3-6}$-cycloalkyl, and R$^3$ denotes hydrogen, fluorine, chlorine, bromine, iodine, C$_{1-6}$-alkyl, C$_{2-6}$-alkenyl, C$_{2-6}$-alkynyl, C$_{3-6}$-cycloalkyl, C$_{3-6}$-cycloalkylidenemethyl, C$_{1-6}$-alkoxy, C$_{3-6}$-cycloalkyl-oxy, C$_{3-6}$-cycloalkyl-C$_{1-3}$-alkoxy, aryl, aryl-C$_{1-3}$-alkyl, heteroaryl, heteroaryl-C$_{1-3}$-alkyl, aryloxy, or aryl-C$_{1-3}$-alkyl-oxy;

or a methyl or methoxy group substituted by 1 to 3 fluorine atoms;

or a C$_{2-4}$-alkyl or C$_{2-4}$-alkoxy group substituted by 1 to 5 fluorine atoms;

or a C$_{1-4}$-alkyl group substituted by a cyano group;

or a C$_{1-4}$-alkyl group substituted by a hydroxy or C$_{1-3}$-alkyloxy group;

or cyano, carboxy, C$_{1-3}$-alkoxycarbonyl, aminocarbonyl, (C$_{1-3}$-alkylamino)carbonyl, di-(C$_{1-3}$-alkyl)aminocarbonyl, pyrrolidin-1-ylcarbonyl, piperidin-1-ylcarbonyl, morpholin-4-ylcarbonyl, piperazin-1-ylcarbonyl, 4-(C$_{1-3}$-alkyl)-piperazin-1-ylcarbonyl, nitro, amino, C$_{1-3}$-alkylamino, di-(C$_{1-3}$-alkyl)amino, (C$_{1-4}$-alkyl)carbonylamino, C$_{1-4}$-alkylsulphonylamino, arylsulphonylamino, aryl-C$_{1-3}$-alkylsulphonylamino, C$_{1-4}$-alkylsulphanyl, C$_{1-4}$-alkylsulphinyl, C$_{1-4}$-alkylsulphonyl, arylsulphenyl, arylsulphinyl or arylsulphonyl, or has a meaning selected from the group A, and R$^4$ and R$^5$, which may be identical or different, represent hydrogen, fluorine, chlorine, bromine, C$_{1-3}$-alkyl, C$_{1-3}$-alkoxy, a methyl or methoxy group substituted by 1 to 3 fluorine atoms, or R$^3$ together with R$^4$, if they are bound to adjacent carbon atoms, may also represent a straight-chain C$_{3-5}$-alkylene, a methylenedioxy or difluoromethylenedioxy bridge, and R$^6$, R$^{7a}$, R$^{7b}$, and R$^{7c}$ independently of one another have a meaning selected from the group consisting of hydrogen, (C$_{1-18}$-alkyl)carbonyl, (C$_{1-18}$-alkyl)oxycarbonyl, arylcarbonyl and aryl-(C$_{1-3}$-alkyl)-carbonyl, A is selected from the group consisting of tetrahydrofuran-3-yloxy, tetrahydropyran-3-yloxy, tetrahydropyran-4-yloxy, tetrahydrofuranyl-C$_{1-3}$-alkoxy, tetrahydropyranyl-C$_{1-3}$-alkoxy, pyrrolidin-3-yloxy, piperidin-3-yloxy, piperidin-4-yloxy group, and pyrrolidin-3-yloxy, piperidin-3-yloxy- and piperidin-4-yloxy, while in the latter three groups the nitrogen atom may be substituted by C$_{1-4}$-alkyl, formyl, C$_{1-4}$-alkyl-carbonyl, C$_{1-4}$-alkylsulphonyl, cyano, aminocarbonyl, (C$_{1-4}$-alkyl)-aminocarbonyl, di-(C$_{1-4}$-alkyl)-aminocarbonyl or (C$_{1-4}$-alkyl)-oxycarbonyl, while the aryl groups mentioned in the definition of the above groups are meant to indicate phenyl or naphthyl groups which may be mono- or disubstituted independently of one another by R$_h$, while the substituents may be identical or different and R$_h$ denotes a fluorine, chlorine, bromine, iodine, C$_{1-3}$-alkyl, difluoromethyl, trifluoromethyl, C$_{1-3}$-alkoxy, difluoromethoxy, trifluoromethoxy or cyano, and the heteroaryl groups mentioned in the definition of the above-mentioned groups are meant to indicate a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, while the above-mentioned heteroaryl groups may be mono- or disubstituted by R$_h$, while the substituents may be identical or different and R$_h$ is as hereinbefore defined, while, unless otherwise stated, the above-mentioned alkyl groups may be straight-chain or branched, or a tautomer, or stereoisomer thereof, or mixtures thereof or a salt thereof.

2. A compound of claim 1, wherein

R$^1$ denotes 2-propyn-1-yl, 2-butyn-1-yl, tetrahydrofuran-3-yl, tetrahydropyran-3-yl, tetrahydropyran-4-yl, tetrahydrofuranylmethyl or tetrahydropyranylmethyl, or, if R$^3$ (a) is selected from the group consisting of tetrahydrofuran-3-yloxy, tetrahydropyran-3-yloxy, tetrahydropyran-4-yloxy, tetrahydrofuranylmethyloxy and tetrahydropyranylmethyloxy, or (b) together with $R^4$ denotes a difluoromethylenedioxy bridge, or, (c) denotes cylopropyloxy, cyclobutyloxy, cyclopentyloxy or cyclopropylidenemethyl and $R^4$ simultaneously denotes fluorine, then $R^1$ may also represent isopropyl, and $R^2$ denotes methyl or trifluoromethyl, and $R^3$ denotes hydrogen, fluorine, chlorine, methyl, ethyl, isopropyl, tert.-butyl, 2-cyano-2-propyl, difluoromethyl, trifluoromethyl, cyclopropyl, cyclobutyl, cyclopentyl, methoxy, ethoxy, isopropoxy, difluoromethoxy, trifluoromethoxy, 1,1,2,2-tetrafluoroethoxy, cylopropyl-oxy, cyclobutyl-oxy, cyclopentyl-oxy, tetrahydrofuran-3-yloxy, tetrahydropyran-3-yloxy, tetrahydropyran-4-yloxy, tetrahydrofuranylmethyloxy, tetrahydropyranylmethyloxy, methylsulphanyl, 2-methyl-1-propen-1-yl, cyclopropylidenemethyl, ethynyl, phenyl, fluorophenyl, pyridyl or methylthiazolyl, and $R^4$ denotes hydrogen or fluorine, or $R^3$ together with $R^4$, if they are bound to adjacent carbon atoms, may also represent a 1,3-propylene, methylenedioxy or difluoromethylenedioxy bridge, and $R^5$ denotes hydrogen and $R^6$ denotes hydrogen, $(C_{1-8}$-alkyl)oxycarbonyl or $C_{1-8}$-alkylcarbonyl, or a tautomer, or stereoisomer thereof, or mixtures thereof or a salt thereof.

3. A compound of claim 1,
wherein
$R^1$ denotes 2-propyn-1-yl, 2-butyn-1-yl, tetrahydrofuran-3-yl, tetrahydropyran-4-yl or tetrahydrofuran-2-ylmethyl or,
if $R^3$
is selected from the group consisting of tetrahydrofuran-3-yloxy, tetrahydropyran-4-yloxy and tetrahydrofuranylmethyloxy,
then $R^1$ may also represent isopropyl,
$R^2$ denotes methyl,
$R^3$ denotes methyl, ethyl, methoxy, ethoxy, difluoromethoxy, tetrahydrofuran-3-yloxy, tetrahydropyran-4-yloxy or tetrahydrofuranylmethyloxy,
$R^4$ denotes hydrogen or fluorine,
$R^5$ denotes hydrogen and
$R^6$ denotes hydrogen, methoxycarbonyl or ethoxycarbonyl,
the tautomers, the stereoisomers, the mixtures thereof and the salts thereof.

4. A compound of claim 1,
wherein
$R^1$ denotes tetrahydrofuran-3-yl or tetrahydropyran-4-yl,
$R^2$ denotes methyl,
$R^3$ denotes methyl, ethyl, methoxy, ethoxy or difluoromethoxy,
$R^4$ denotes hydrogen or fluorine,
$R^5$ denotes hydrogen,
$R^6$ denotes hydrogen, methoxycarbonyl or ethoxycarbonyl and
$R^{7a}$, $R^{7b}$ and $R^{7c}$ denote hydrogen,
or a tautomer, or stereoisomer thereof, or mixtures thereof or a salt thereof.

5. A compound of claim 1 selected from the group consisting of:

(a) 1-(2-propyn-1-yl)-3-(β-D-glucopyranosyloxy)-4-(4-ethylbenzyl)-5-methyl-1H-pyrazole, (b) 1-(2-propyn-1-yl)-3-(6-O-methoxycarbonyl-β-D-glucopyranosyloxy)-4-(4-ethylbenzyl)-5-methyl-1H-pyrazole, (c) 1-((S)-tetrahydrofuran-3-yl)-3-(β-D-glucopyranosyloxy)-4-(4-ethylbenzyl)-5-methyl-1H-pyrazole, (d) 1-(tetrahydropyran-4-yl)-3-(β-D-glucopyranosyloxy)-4-(4-ethylbenzyl)-5-methyl-1H-pyrazole, (e) 1-isopropyl-3-(β-D-glucopyranosyloxy)-4-[4-((S)-tetrahydrofuran-3-yloxy)benzyl]-5-methyl-1H-pyrazole, (f) 1-isopropyl-3-(β-D-glucopyranosyloxy)-4-[4-((R)-tetrahydrofuran-3-yloxy)benzyl]-5-methyl-1H-pyrazole, (g) 1-(tetrahydropyran-4-yl)-3-(β-D-glucopyranosyloxy)-4-(4-methoxybenzyl)-5-methyl-1H-pyrazole, and the derivatives of (a) to (g), wherein the position corresponding to $R^6$ is, instead of hydrogen, selected from $(C_{1-18}$-alkyl)carbonyl, $(C_{1-18}$-alkyl)oxycarbonyl, arylcarbonyl and aryl-$(C_{1-3}$-alkyl)-carbonyl groups, or a tautomer, or stereoisomer thereof, or mixtures thereof or a salt thereof.

6. A physiologically acceptable salt of the compound according to claim 1 with an inorganic or organic acid.

7. A pharmaceutical composition, containing a compound according to claim 1, together with one or more inert carriers or diluents.

8. A pharmaceutical composition, containing a physiologically acceptable salt according to claim 6, together with one or more inert carriers or diluents.

9. A method for treating a disease or condition which can be influenced by inhibiting the sodium-dependent glucose cotransporter SGLT comprising administering a therapeutically effective amount of at least one compound according to claim 1.

10. A method for treating a disease or condition which can be influenced by inhibiting the sodium-dependent glucose cotransporter SGLT comprising administering a therapeutically effective amount of at least one physiologically acceptable salt according to claim 6.

11. A method for treating a metabolic disorder comprising administering a therapeutically effective amount of at least one compound according to claim 1.

12. A method for treating a metabolic disorder comprising administering a therapeutically effective amount of at least one physiologically acceptable salt according to claim 6.

13. The method according to claim 11, wherein the metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

14. The method according to claim 12, wherein the metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

15. A process for preparing a pharmaceutical composition, wherein a compound according to claim 1 is incorporated in one or more inert carriers or diluents by a non-chemical method.

16. A process for preparing a pharmaceutical composition, wherein a physiologically acceptable salt according to claim 6 is incorporated in one or more inert carriers or diluents by a non-chemical method.

17. A process for preparing a compound of formula I according to claim 1 comprising:
(a) reacting a compound of formula (II):

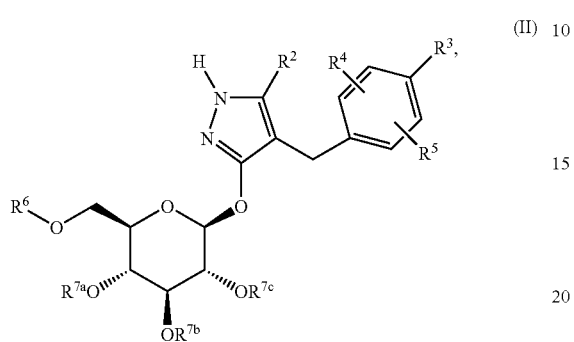

wherein
$R^2$ to $R^6$ and $R^{7a}$, $R^{7b}$, $R^{7c}$ are defined as in claim 1, with a compound of formula (III):

$$Z^1\text{—}R^{1'} \qquad (III),$$

wherein
$R^{1'}$ is defined as for $R^1$ as in claim 1, but does not denote a hydrogen atom, and $Z^1$ denotes a leaving group; and, optionally,
converting the compound thus obtained into a physiologically acceptable salt thereof.

18. A process for preparing a compound of formula I according to claim 1 comprising:
(a) reacting a compound of formula (IV):

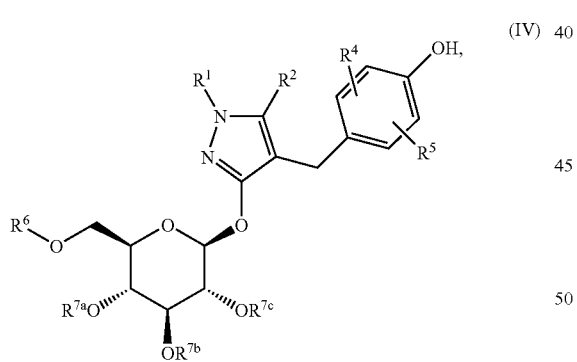

wherein
$R^1$, $R^2$ and $R^4$ to $R^6$ and $R^{7a}$, $R^{7b}$, $R^{7c}$ are defined as in claim 1,
with a compound of formula (V):

$$Z^2\text{—}R^{3'} \qquad (V),$$

wherein
$R^{3'}$ denotes optionally substituted $C_{1-6}$-alkoxy, $C_{3-6}$-cycloalkyl-oxy, $C_{3-5}$-cycloalkyl-$C_{1-3}$-alkoxy or has a meaning selected from the group A, which is as hereinbefore defined, and $Z^2$ denotes a leaving group; and, optionally, converting the compound thus obtained into a physiologically acceptable salt thereof.

19. The process according to claim 18, wherein $Z^2$ is selected from the group consisting of chlorine, bromine, methanesulphonyloxy, p-toluenesulphonyloxy, and hydroxyl.

20. The process according to claim 17 further comprising converting a hydrogen atom by acylation into a corresponding acyl compound, wherein the hydrogen atom is denoted by $R^6$.

21. The process according to claim 18 further comprising converting a hydrogen atom by acylation into a corresponding acyl compound, wherein the hydrogen atom is denoted by $R^6$.

22. The process according to claim 17, further comprising cleaving any protecting group used during the reaction.

23. The process according to claim 18, further comprising cleaving any protecting group used during the reaction.

24. The process according to claim 17, further comprising resolving the compound thus obtained into its stereoisomers.

25. The process according to claim 18, further comprising resolving the compound thus obtained into its stereoisomers.

26. A compound of claim 5, which is a derivative compound of one of (a) to (g) wherein $R^6$ is, instead of hydrogen, ethoxycarbonyl or methoxycarbonyl.

* * * * *